US009644623B2

(12) United States Patent
Mathies et al.

(10) Patent No.: US 9,644,623 B2
(45) Date of Patent: May 9, 2017

(54) FLUID CONTROL STRUCTURES IN MICROFLUIDIC DEVICES

(75) Inventors: Richard A. Mathies, San Francisco, CA (US); William H. Grover, Medford, MA (US); Alison Skelley, Berkeley, CA (US); Eric Lagally, Santa Barbara, CA (US); Chung N. Liu, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 1769 days.

(21) Appl. No.: 12/782,598

(22) Filed: May 18, 2010

(65) Prior Publication Data
US 2010/0224255 A1    Sep. 9, 2010

Related U.S. Application Data

(62) Division of application No. 12/203,800, filed on Sep. 3, 2008, which is a division of application No. (Continued)

(51) Int. Cl.
*C12M 1/34* (2006.01)
*F04B 43/04* (2006.01)
(Continued)

(52) U.S. Cl.
CPC .............. *F04B 43/043* (2013.01); *B01F 5/10* (2013.01); *B01F 11/0071* (2013.01);
(Continued)

(58) Field of Classification Search
CPC ........... B01L 3/5025; B01L 2400/0487; B01L 2400/049; B01L 2400/0638
(Continued)

(56) References Cited

U.S. PATENT DOCUMENTS 3,190,310 A    6/1965  Honsinger
3,352,643 A   11/1967  Ando et al.
(Continued)

FOREIGN PATENT DOCUMENTS

CA    2433145 A1    5/2002
CN    101449089     6/2009
(Continued)

OTHER PUBLICATIONS

Vieider et al. "A Pneumatically actuated micro valve with a silicone rubber membrane for integration with fluid-handling systems." Transducers '95, Jun. 25-29, 1995, pp. 284-286.*
(Continued)

*Primary Examiner* — William H Beisner
(74) *Attorney, Agent, or Firm* — Weaver Austin Villeneuve & Sampson LLP

(57) ABSTRACT

Methods and apparatus for implementing microfluidic analysis devices are provided. A monolithic elastomer membrane associated with an integrated pneumatic manifold allows the placement and actuation of a variety of fluid control structures, such as structures for pumping, isolating, mixing, routing, merging, splitting, preparing, and storing volumes of fluid. The fluid control structures can be used to implement a variety of sample introduction, preparation, processing, and storage techniques.

13 Claims, 14 Drawing Sheets

Related U.S. Application Data

10/750,533, filed on Dec. 29, 2003, now Pat. No. 7,445,926.

(60) Provisional application No. 60/475,013, filed on May 30, 2003, provisional application No. 60/437,262, filed on Dec. 30, 2002.

(51) Int. Cl.
| | |
|---|---|
| *B01F 5/10* | (2006.01) |
| *B01F 11/00* | (2006.01) |
| *B01F 13/00* | (2006.01) |
| *C12Q 1/68* | (2006.01) |
| *F04B 43/06* | (2006.01) |
| *F16K 99/00* | (2006.01) |
| *B01L 3/00* | (2006.01) |
| *B01L 7/00* | (2006.01) |
| *G01N 35/00* | (2006.01) |

(52) U.S. Cl.
CPC ...... *B01F 13/0059* (2013.01); *B01L 3/50273* (2013.01); *B01L 3/502707* (2013.01); *B01L 3/502738* (2013.01); *C12Q 1/6806* (2013.01); *C12Q 1/689* (2013.01); *F04B 43/06* (2013.01); *F16K 99/0001* (2013.01); *B01L 3/5025* (2013.01); *B01L 7/52* (2013.01); *B01L 2200/10* (2013.01); *B01L 2300/0654* (2013.01); *B01L 2300/0803* (2013.01); *B01L 2300/087* (2013.01); *B01L 2300/088* (2013.01); *B01L 2300/0816* (2013.01); *B01L 2300/0819* (2013.01); *B01L 2300/0861* (2013.01); *B01L 2300/0887* (2013.01); *B01L 2300/1827* (2013.01); *B01L 2400/0409* (2013.01); *B01L 2400/0421* (2013.01); *B01L 2400/0487* (2013.01); *B01L 2400/0638* (2013.01); *B01L 2400/0655* (2013.01); *C12Q 2565/629* (2013.01); *G01N 35/00069* (2013.01); *Y10T 137/0318* (2015.04); *Y10T 137/2224* (2015.04); *Y10T 137/87716* (2015.04)

(58) Field of Classification Search
USPC ...................................................... 435/288.5
See application file for complete search history.

(56) References Cited

U.S. PATENT DOCUMENTS

| | | | |
|---|---|---|---|
| 3,433,257 A | 3/1969 | Jensen | |
| 3,568,692 A | 3/1971 | Metzger et al. | |
| 3,610,274 A | 10/1971 | Levesque et al. | |
| 3,636,334 A | 1/1972 | Svoboda | |
| 3,768,521 A | 10/1973 | Brychta et al. | |
| 4,304,257 A | 12/1981 | Webster | |
| 4,357,675 A | 11/1982 | Freyman | |
| 4,558,845 A | 12/1985 | Hunkapiller | |
| 4,703,913 A | 11/1987 | Hunkapiller | |
| 4,963,498 A | 10/1990 | Hillman et al. | |
| 5,157,284 A | 10/1992 | O'Connell et al. | |
| 5,376,252 A | 12/1994 | Ekström et al. | |
| 5,453,163 A | 9/1995 | Yan | |
| 5,571,410 A | 11/1996 | Swedberg et al. | |
| 5,587,128 A | 12/1996 | Wilding et al. | |
| 5,609,919 A | 3/1997 | Yuan et al. | |
| 5,635,358 A | 6/1997 | Wilding et al. | |
| 5,639,428 A | 6/1997 | Cottingham | |
| 5,660,370 A * | 8/1997 | Webster ................. 251/129.17 |
| 5,705,813 A | 1/1998 | Apffel et al. | |
| 5,726,026 A | 3/1998 | Wilding et al. | |
| 5,741,462 A | 4/1998 | Nova et al. | |
| 5,750,015 A | 5/1998 | Soane et al. | |
| 5,770,029 A | 6/1998 | Nelson et al. | |
| 5,775,371 A | 7/1998 | Pan et al. | |
| 5,842,787 A | 12/1998 | Kopf-sill et al. | |
| 5,856,174 A | 1/1999 | Lipshutz et al. | |
| 5,863,502 A | 1/1999 | Southgate et al. | |
| 5,885,470 A | 3/1999 | Parce et al. | |
| 5,900,130 A | 5/1999 | Benvegnu | |
| 5,908,552 A | 6/1999 | Zimmerman et al. | |
| 5,922,591 A | 7/1999 | Anderson et al. | |
| 5,942,443 A | 8/1999 | Parce et al. | |
| 5,971,158 A | 10/1999 | Yager et al. | |
| 6,001,229 A | 12/1999 | Ramsey | |
| 6,007,690 A | 12/1999 | Nelson et al. | |
| 6,007,775 A | 12/1999 | Yager | |
| 6,010,607 A | 1/2000 | Ramsey | |
| 6,048,100 A | 4/2000 | Thrall et al. | |
| 6,056,860 A | 5/2000 | Amigo et al. | |
| 6,073,482 A | 6/2000 | Moles | |
| 6,074,827 A | 6/2000 | Nelson et al. | |
| 6,103,199 A | 8/2000 | Bjornson et al. | |
| 6,120,184 A | 9/2000 | Laurence et al. | |
| 6,136,212 A | 10/2000 | Mastrangelo et al. | |
| 6,168,948 B1 | 1/2001 | Anderson et al. | |
| 6,176,962 B1 | 1/2001 | Soane et al. | |
| 6,190,616 B1 | 2/2001 | Jovanovich et al. | |
| 6,197,595 B1 | 3/2001 | Anderson et al. | |
| 6,207,031 B1 | 3/2001 | Adourian et al. | |
| 6,235,471 B1 | 5/2001 | Knapp et al. | |
| 6,238,538 B1 | 5/2001 | Parce et al. | |
| 6,251,343 B1 | 6/2001 | Dubrow et al. | |
| 6,280,589 B1 | 8/2001 | Manz et al. | |
| 6,319,476 B1 | 11/2001 | Victor, Jr. et al. | |
| 6,321,791 B1 | 11/2001 | Chow | |
| 6,322,683 B1 | 11/2001 | Wolk et al. | |
| 6,348,318 B1 | 2/2002 | Valkirs | |
| 6,379,929 B1 | 4/2002 | Burns et al. | |
| 6,403,338 B1 | 6/2002 | Knapp et al. | |
| 6,408,878 B2 | 6/2002 | Unger et al. | |
| 6,423,536 B1 | 7/2002 | Jovanovich et al. | |
| 6,429,025 B1 | 8/2002 | Parce et al. | |
| 6,432,290 B1 | 8/2002 | Harrison et al. | |
| 6,454,924 B2 | 9/2002 | Jedrzejewski et al. | |
| 6,489,112 B1 | 12/2002 | Hadd et al. | |
| 6,520,753 B1 | 2/2003 | Grosjean et al. | |
| 6,521,188 B1 | 2/2003 | Webster | |
| 6,524,456 B1 | 2/2003 | Ramsey et al. | |
| 6,532,997 B1 | 3/2003 | Bedingham et al. | |
| 6,533,914 B1 | 3/2003 | Liu | |
| 6,537,757 B1 | 3/2003 | Langmore et al. | |
| 6,544,734 B1 | 4/2003 | Briscoe et al. | |
| 6,551,839 B2 | 4/2003 | Jovanovich et al. | |
| 6,581,441 B1 | 6/2003 | Paul | |
| 6,605,454 B2 | 8/2003 | Barenburg et al. | |
| 6,613,525 B2 | 9/2003 | Nelson et al. | |
| 6,614,228 B2 | 9/2003 | Hofmann et al. | |
| 6,618,679 B2 | 9/2003 | Loehrlein | |
| 6,623,613 B1 | 9/2003 | Mathies et al. | |
| 6,627,446 B1 | 9/2003 | Roach et al. | |
| 6,629,820 B2 | 10/2003 | Kornelsen | |
| 6,632,619 B1 | 10/2003 | Harrison et al. | |
| 6,632,655 B1 | 10/2003 | Mehta et al. | |
| 6,663,833 B1 | 12/2003 | Stave et al. | |
| D486,156 S | 2/2004 | Lee et al. | |
| 6,685,442 B2 | 2/2004 | Chinn et al. | |
| 6,705,345 B1 | 3/2004 | Bifano | |
| D488,818 S | 4/2004 | Lee et al. | |
| 6,752,922 B2 | 6/2004 | Huang et al. | |
| 6,764,648 B1 | 7/2004 | Roach et al. | |
| 6,782,746 B1 | 8/2004 | Hasselbrink et al. | |
| 6,786,708 B2 | 9/2004 | Brown et al. | |
| 6,787,111 B2 | 9/2004 | Roach et al. | |
| 6,793,753 B2 | 9/2004 | Unger et al. | |
| 6,802,342 B2 | 10/2004 | Fernandes et al. | |
| 6,803,019 B1 | 10/2004 | Bjornson et al. | |
| 6,824,663 B1 | 11/2004 | Boone | |
| 6,829,753 B2 | 12/2004 | Lee et al. | |
| 6,852,287 B2 | 2/2005 | Ganesan | |
| 6,870,185 B2 | 3/2005 | Roach et al. | |
| 6,883,774 B2 | 4/2005 | Nielsen et al. | |

(56) References Cited

U.S. PATENT DOCUMENTS

| | | |
|---|---|---|
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,097,809 B2 | 8/2006 | Van Dam et al. |
| 7,198,759 B2 | 4/2007 | Bryning et al. |
| 7,261,812 B1 | 8/2007 | Karp et al. |
| 7,279,146 B2 | 10/2007 | Nassef et al. |
| 7,282,361 B2 | 10/2007 | Hodge |
| 7,312,611 B1 | 12/2007 | Harrison et al. |
| 7,323,305 B2 | 1/2008 | Leamon et al. |
| 7,438,856 B2 | 10/2008 | Jedrzejewski et al. |
| 7,445,926 B2 | 11/2008 | Mathies et al. |
| 7,488,603 B2 | 2/2009 | Gjerde et al. |
| 7,622,081 B2 | 11/2009 | Chou et al. |
| 7,745,207 B2 | 6/2010 | Jovanovich et al. |
| 7,763,453 B2 | 7/2010 | Clemmens et al. |
| 7,766,033 B2 | 8/2010 | Mathies et al. |
| 7,799,533 B2 | 9/2010 | Hinuma et al. |
| 7,867,763 B2 | 1/2011 | Facer et al. |
| 8,105,553 B2 | 1/2012 | Grossman et al. |
| 8,257,666 B2 | 9/2012 | Quake et al. |
| 8,286,665 B2 | 10/2012 | Mathies et al. |
| 8,420,318 B2 | 4/2013 | Mathies et al. |
| 8,454,906 B2 | 6/2013 | Mathies et al. |
| 8,841,116 B2 | 9/2014 | Mathies et al. |
| 2001/0041357 A1 | 11/2001 | Fouillet et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0119480 A1 | 8/2002 | Weir et al. |
| 2002/0119482 A1 | 8/2002 | Nelson et al. |
| 2002/0127736 A1 | 9/2002 | Chou et al. |
| 2002/0139084 A1 | 10/2002 | Tobolka |
| 2002/0144738 A1 | 10/2002 | Unger et al. |
| 2002/0148992 A1 | 10/2002 | Hayenga et al. |
| 2002/0160361 A1 | 10/2002 | Loehrlein et al. |
| 2002/0166585 A1 | 11/2002 | O'Connor et al. |
| 2002/0187560 A1 | 12/2002 | Pezzuto et al. |
| 2002/0195152 A1 | 12/2002 | Fernandes et al. |
| 2003/0008308 A1 | 1/2003 | Enzelberger et al. |
| 2003/0021734 A1 | 1/2003 | Vann et al. |
| 2003/0070677 A1 | 4/2003 | Handique et al. |
| 2003/0217923 A1 | 11/2003 | Harrison et al. |
| 2004/0014091 A1 | 1/2004 | Duck et al. |
| 2004/0037739 A1 | 2/2004 | Mcneely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086872 A1 | 5/2004 | Childers et al. |
| 2004/0132170 A1 | 7/2004 | Storek et al. |
| 2004/0151629 A1 | 8/2004 | Pease et al. |
| 2004/0197845 A1 | 10/2004 | Hassibi et al. |
| 2004/0209354 A1 | 10/2004 | Mathies et al. |
| 2004/0224380 A1 | 11/2004 | Chou et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0155861 A1 | 7/2005 | Guzman |
| 2005/0161326 A1 | 7/2005 | Morita et al. |
| 2005/0161669 A1 | 7/2005 | Jovanovich et al. |
| 2005/0224134 A1 | 10/2005 | Yin et al. |
| 2005/0224352 A1 | 10/2005 | Harrison et al. |
| 2005/0241941 A1 | 11/2005 | Parce et al. |
| 2005/0255003 A1 | 11/2005 | Summersgill et al. |
| 2005/0287572 A1 | 12/2005 | Mathies et al. |
| 2006/0027456 A1 | 2/2006 | Harrison et al. |
| 2006/0057209 A1 | 3/2006 | Chapman et al. |
| 2006/0073484 A1 | 4/2006 | Mathies et al. |
| 2006/0076068 A1 | 4/2006 | Young et al. |
| 2006/0140051 A1 | 6/2006 | Kim et al. |
| 2006/0163143 A1 | 7/2006 | Chirica et al. |
| 2006/0186043 A1 | 8/2006 | Covey et al. |
| 2006/0266645 A1 | 11/2006 | Chen et al. |
| 2007/0017812 A1 | 1/2007 | Bousse |
| 2007/0034025 A1 | 2/2007 | Pant et al. |
| 2007/0092914 A1 | 4/2007 | Griffiths et al. |
| 2007/0105163 A1 | 5/2007 | Grate et al. |
| 2007/0122819 A1 | 5/2007 | Wu et al. |
| 2007/0175756 A1 | 8/2007 | Nguyen et al. |
| 2007/0184463 A1 | 8/2007 | Molho et al. |
| 2007/0202531 A1 | 8/2007 | Grover |
| 2007/0237686 A1 | 10/2007 | Mathies et al. |
| 2007/0238109 A1 | 10/2007 | Min et al. |
| 2007/0248958 A1 | 10/2007 | Jovanovich et al. |
| 2007/0297947 A1 | 12/2007 | Sommers et al. |
| 2008/0014576 A1 | 1/2008 | Jovanovich et al. |
| 2008/0014589 A1 | 1/2008 | Link et al. |
| 2008/0047836 A1 | 2/2008 | Strand et al. |
| 2008/0124723 A1 | 5/2008 | Dale et al. |
| 2008/0164155 A1 | 7/2008 | Pease et al. |
| 2008/0179255 A1 | 7/2008 | Jung et al. |
| 2008/0237146 A1 | 10/2008 | Harrison et al. |
| 2008/0281090 A1 | 11/2008 | Lee et al. |
| 2008/0302732 A1 | 12/2008 | Soh et al. |
| 2008/0311585 A1 | 12/2008 | Gao et al. |
| 2009/0004494 A1 | 1/2009 | Blenke et al. |
| 2009/0035770 A1 | 2/2009 | Mathies et al. |
| 2009/0053799 A1 | 2/2009 | Chang-yen et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0181411 A1 | 7/2009 | Battrell et al. |
| 2009/0253181 A1 | 10/2009 | Vangbo et al. |
| 2009/0286327 A1 | 11/2009 | Cho et al. |
| 2009/0311804 A1 | 12/2009 | Mcbrady et al. |
| 2010/0068723 A1 | 3/2010 | Jovanovich et al. |
| 2010/0165784 A1 | 7/2010 | Jovanovich et al. |
| 2010/0224255 A1 | 9/2010 | Mathies et al. |
| 2010/0252123 A1 | 10/2010 | Mathies et al. |
| 2010/0285975 A1 | 11/2010 | Mathies et al. |
| 2010/0303687 A1 | 12/2010 | Blaga et al. |
| 2010/0326826 A1 | 12/2010 | Harrison et al. |
| 2011/0005932 A1 | 1/2011 | Jovanovich et al. |
| 2011/0020920 A1 | 1/2011 | Mathies et al. |
| 2011/0027913 A1 | 2/2011 | Bau et al. |
| 2011/0039303 A1 | 2/2011 | Jovanovich et al. |
| 2011/0048945 A1 | 3/2011 | Harrison et al. |
| 2011/0076735 A1 | 3/2011 | Jovanovich et al. |
| 2012/0142010 A1 | 6/2012 | Mathies et al. |
| 2012/0164627 A1 | 6/2012 | Battrell et al. |
| 2012/0276544 A1 | 11/2012 | Quake et al. |

FOREIGN PATENT DOCUMENTS

| | | |
|---|---|---|
| CN | 102416350 | 4/2012 |
| EP | 0459241 B1 | 12/1991 |
| EP | 0527905 B1 | 11/1995 |
| EP | 0637999 A1 | 12/1998 |
| EP | 1065378 B1 | 4/2002 |
| EP | 1411340 A2 | 4/2004 |
| EP | 1411340 A3 | 5/2004 |
| EP | 1774042 | 4/2007 |
| EP | 1345697 B1 | 6/2007 |
| EP | 1658890 B1 | 5/2008 |
| EP | 2029921 | 3/2009 |

(56) References Cited

FOREIGN PATENT DOCUMENTS

| EP | 1345551 B1 | 4/2009 |
|---|---|---|
| EP | 2404676 | 11/2012 |
| JP | 2007/506430 A | 7/1995 |
| JP | 408327594 A | 12/1996 |
| JP | 2001/500966 | 1/2001 |
| JP | 2001/521818 A | 11/2001 |
| JP | 2002/3701200 A | 12/2002 |
| JP | 2006-512092 | 4/2006 |
| JP | 2008-500836 | 1/2008 |
| JP | 2009-530569 | 8/2009 |
| JP | 2011-234728 | 11/2011 |
| WO | 93/22053 | 4/1993 |
| WO | 93/22053 | 11/1993 |
| WO | 96/04547 A1 | 2/1996 |
| WO | 98/10277 | 3/1998 |
| WO | 99/22868 | 10/1998 |
| WO | 98/52691 A1 | 11/1998 |
| WO | 98/53300 A2 | 11/1998 |
| WO | 98/53300 A3 | 11/1998 |
| WO | 99/36766 A1 | 7/1999 |
| WO | 99/40174 A1 | 8/1999 |
| WO | 00/40712 A1 | 7/2000 |
| WO | 00/60362 A1 | 10/2000 |
| WO | 00/61198 A1 | 10/2000 |
| WO | 00/72970 | 12/2000 |
| WO | 01/32930 A1 | 5/2001 |
| WO | 01/38865 A1 | 5/2001 |
| WO | 01/85341 A1 | 11/2001 |
| WO | 02/41994 | 5/2002 |
| WO | 02/43615 A2 | 6/2002 |
| WO | 02/43864 | 6/2002 |
| WO | 02/043615 A3 | 3/2003 |
| WO | 03/085379 A2 | 10/2003 |
| WO | 03/085379 A3 | 10/2003 |
| WO | 2004/061085 | 7/2004 |
| WO | 2004/098757 A2 | 11/2004 |
| WO | 2005/075081 A1 | 8/2005 |
| WO | 2005/118867 | 12/2005 |
| WO | 2006/032044 | 3/2006 |
| WO | 2004/098757 A3 | 5/2006 |
| WO | 2007/082480 A1 | 7/2007 |
| WO | 2007/109375 | 9/2007 |
| WO | 2008/039875 A1 | 4/2008 |
| WO | 2008/052138 | 5/2008 |
| WO | 2008/115626 A2 | 9/2008 |
| WO | 2008/115626 A3 | 9/2008 |
| WO | 2009/015296 | 1/2009 |
| WO | 2009/129415 A1 | 10/2009 |
| WO | 2010/041174 A1 | 4/2010 |

OTHER PUBLICATIONS

U.S. Appl. No. 12/026,510, filed Feb. 5, 2008, Jovanovich et al.
U.S. Appl. No. 12/820,390, filed Jun. 22, 2010, Harrison et al.
U.S. Appl. No. 12/845,650, filed Jul. 28, 2010, Jovanovich et al.
U.S. Appl. No. 12/949,623, filed Nov. 18, 2010, Kobrin et al.
Mathies, et al., U.S. Appl. No. 12/819,094, titled "Multiplexed Latching Valves for Microfluidic Devices and Processors," filed Jun. 18, 2010.
Japanese Office Action mailed Mar. 1, 2011 for Appln. No. 2007-515379.
European Office Action mailed Apr. 7, 2011 from Application No. 05804847.1.
Coleman, et al. A sequential injection microfluidic mixing strategy. Microfluidics and Nanofluidics. 2005;319-327.
Ericson, et al. Electroosmosis- and Pressure-Driven Chromatography in Chips Using Continuous Beds. Analytical Chemistry. 2000;72(1):81-87.
International search report and written opinion dated Mar. 24, 2011 for PCT Application No. US2010/58227.
International search report and written opinion dated Sep. 1, 2010 for PCT Application No. US2010/040490.
International search report dated Oct. 6, 2010 for PCT Application No. US10/37545.
International search report dated Apr. 5, 2001 for PCT Application No. CA2000/01421.
International search report dated May 14, 2010 for PCT Application No. US2009/06640.
International search report dated Jul. 11, 2008 for PCT Application No. US07/61573.
International search report dated Jul. 30, 2010 for PCT Application No. US2010/36464.
International search report dated Aug. 18, 2009 for PCT Application No. US09/00419.
International search report dated Aug. 26, 2004 PCT Application No. US2003/41466.
International search report dated Sep. 25, 2007 for PCT Application No. US2007/02721.
International Search Report for PCT/US2005/033347—Annex to Form PCT/ISA/206.
Jacobson, et al. Electrokinetic Focusing in Microfabricated Channel Structures. Anal. Chem., 1997, 69 (16), pp. 3212-3217.
Japanese Office Action dated Dec. 21, 2010 for Application No. JP2001-540363 (in Japanese with English translation).
Japanese Office Action dated Apr. 27, 2010 for Application No. JP2001-540363 (in Japanese with English translation).
MiliGat pump user manual, version 2.12, published 2005, pp. 1-28.
Norris, et al. Fully-integrated, multiplexed STR-based human identification using a single microfluidic chip and automated instrument. Available at http://www.promega.com/geneticidproc/ussymp20proc/oralpresentations/landersbienvenue.pdf . Accessed Jun. 2, 2010.
Mathies, et al., U.S. Appl. No. 12/670,377, titled "Microfabricated Droplet Generator for Single Molecule/Cell Genetic Analysis in Engineered Monodispersed Emulsions," filed Jan. 22, 2010.
European Supplemental International Search Report dated Dec. 18, 2009.
Kamel, T., et al., "Integrated Hydrogenated Amorphous Si Photodiode Detector for Microfluidic Bioanalytical Devices," Analytical Chemistry, 2003, vol. 75, pp. 5300-5305.
Koch, et al. "Optical flow cell multichannel immunosensor for the detection of biological warefare agents" Biosensors & Bioelectrics 14 (2000) pp. 779-784.
Yacoub-George, et al. "Chemiluminescence multichannel immunosensor for biodetection" Analytica Chimica Acta 457 (2002) pp. 3-12.
Delehanty, et al. "A Microarray Immunoassay for Simultaneous Detection of Proteins and Bacteria" Anal. Chem. 2002, 74, pp. 5681-5687.
Rowe-Taitt, et al., "Simultaneous detection of six biohazardous agents using a planar waveguicle array biosensor", Biosensors & Bioelectronics 15 (2000) pp. 5798-589.
Rowe, et al., "Array Biosensor for Simultaneous Identification of Bacterial, Viral and Protein Analytes" Anal. Chem. 1999, 71 pp. 3846-3852.
O'Maiiony, et al. "A real time PCR assay for the detection and quantitation of *Mycobacterium avium* subsp. Paratuberculosis using SYBR Green and the Light Cycler" Journal of Microbiological Methods 51 (2002) pp. 283-293.
Papadelli, et al., "Rapid detection and identification of *Streptococcus macedonicus* by species-specific PCR and DNA hybridisation" International Journal of Food Microbiology 81 (2003) pp. 231-239.
Hansen, et al. "Polymerase chain reaction assay for the detection of Bacillus cereus group cells" FEMS Microbiology Letters 202 (2001) pp. 209-213.
Kong, et al."Rapid detection of six types of bacterial pathogens in marine waters by multiplex PCR" Walter Research 36 (2002) pp. 2802-2812.
Nataro, et al. "Diarrheagenic *Escherichia coli*" Clinical MicroBiology Reviews, Jan. 1998 pp. 142-201.
Kimura, et al. Restriction-Site-Specific PCR as a Rapid Test to Detect Enterohemorrhagic *Escherichia coli* O157:H7 Strains in Environmental Samples; Applied and Environmental Microbiology Jun. 2000 (pp. 2513-2519).

(56) References Cited

OTHER PUBLICATIONS

Peng, et al. "Immuno-capture PCR for detection of Aeromonas hydrophila" Journal of Microbiological Methods 49 (2002) pp. 335-338.
Call, et al. "Detecting and genotyping Escherichia coli O157:H7 using multiplexed PCR and nucleic acid microarrays" International Journal of Food Microbiology 67 (2001) pp. 71-80.
White, et al., "Flash detection/identification of pathogens, bacterial spores and bioterrorism agent biomarker from clinical and environmental matrices" Journal of Microbiological Methods 48 (2002) pp. 139-147.
Ruan, et al., "Immunobiosensor Chips for Detection of Escherichia coli O157:H7 Using Electrochemical Impedance Spectroscopy" Anal. Chem 2002 74 pp. 4814-4820.
Gau, et al., "A MEMS based amperometric detector for E. coli bacteria using self-assembled monolayers" Biosensors & Bioelectronics 16 (2001) pp. 745-755.
Kourentzi, et al., "Microbial identification by immunohybridization assay of artificial RNA labels" Journal of Microbiological Methods 49 (2002) pp. 301-306.
Belgrader, et al. "Rapid PCR for Identity Testing Using a Battery-Powered Miniature Thermal Cycler" J Forensic Sci. 1998, pp. 315-319.
Belgrader, et al. "A Minisonicator to Rapidly Disrupt Bacterial Spores for DNA Analysis" Anal. Chem 1999 pp. 4232-4236.
Belgrader, et al. "PCR Detection of Bacteria in Seven Minutes" Science Magazine vol. 284, Issue 5413 (1999) pp. 449-450.
Verlee, et al. "Fluid Circuit Technology: Integrated Interconnect Technology for Miniature Fluidic Devices" Abbott Laboratories Hospital Division, Abbott Park, IL (1996) pp. 9-14.
Dodson, et al., "Fluidics Cube for Biosensor Miniaturization" Anal. Chem 2001 pp. 3776-3780.
Walt, et al., "Biological Warefare" Analytical Chemistry (2000) pp. 739-746.
Yang, et al. "An Integrated Stacked Microlaboratory for Biological Agent Detection with DNA and Immunoassays" Biosensors & Bioelectronics 17 (2002) pp. 605-618.
Reyes, et al. "Micro Total Analysis Systems. 1. Introduction Theory and Technology" Anal Chem (2002) pp. 2623-2636.
Auroux, et al. "Micro Total Analysis Systems 2. Analytical Standard Operations and Applications" Anal. Chem 2002 pp. 2637-2652.
Manz, et al. "Miniaturized Total Chemical Analysis Systems: A Novel Concept for Chemical Sensing" Sensors & Actuators (1990) pp. 244-248.
Jacobson, et al. "High-Speed Separations on a Microchip" Anal. Chem 1994 pp. 1114-1118.
Soper, et al. "Polymeric Microelectro-mechanical Systems" Anal. Chem (2000) pp. 643-651.
Shi, et al. "Radial Capillary Array Electrophoresis Microplate and Scanner for High Performance Nucleic Acid Analysis" Anal. Chem 1999 pp. 5354-5361.
Waters, et al. "Microchip Device for Cell Lysis, Multiplex PCR Amplification, and Electrophoretic Sizing" Anal. Chem 1999 pp. 158-162.
Jacobson, et al. "Integrated Microdevice for DNA Restriction Fragment Analysis" Anal. Chem 1996 pp. 720-723.
Burns, et al. "An Integrated Nanoliter DBA Analysis Device" Science Magazine 1998 pp. 484-487.
Duffy, et al. "Rapid Prototyping of Microfluidic Systems in Poly(dimethylsiloxane)" Anal. Chem 1998 (pp. 4974-4984.
Quake, et al. "From Micro-to Nanofabrication with Soft Materials" Science Magazine (2000) pp. 1536-1540.
Medintz, et al. "High-Performance Genetic Analysis Using Microfabricated Capillary Array Electoporesis Microplates" Electrophoresis 2001 pp. 3845-3856.
Medintz, et al. "High-Performance Multiplex SNP Analysis of Three Hemochromatosis-Related Mutations with Capillary Array Electrophoresis Microplates" Genome Research 2001 pp. 413-421.
Medintz, et al. "Genotyping Energy-Transfer Cassette Labeled Short Tandem Repeat Amplicons with Capillary Array Electrophoresis Microchannel Plates" Clinical Chemistry (2001) pp. 1614-1621.
Webster, et al. "Monolithic Capillary Electrophoresis Device with Integrated Fluorescence Detector" Anal. Chem 2001 pp. 1622-1626.
Kamel, et al. "Integrated Amorphous Silicon Photodiode Detector for Microfabricated Capillary Electrophoresis Devices" Micro Total Analysis Systems 2002 pp. 257-259.
Kuhnert, et al. "Detection System for Escherichia coli-Specific Virulence Genes: Absence of Virulence Determinants in B and C Strains" applied and Environmental Microbiology (1997) pp. 703-709.
Stumpfle, et al. "Absence of DNA sequence homology with genes of the Excherichia coli hemB locus in Shiga-toxin producing E. coli (STEC) 0157 Strains" FEMS Microbiology Letters 174 (1999) pp. 97-103.
Chandler, et al. "Automated immunomagnetic separation and microarray detection of E. coli 0157:H7 from poultry carcass rinse" International Journal of Food Microbiology 70 (2001) pp. 143-154.
Tian, et al. "Evaluation of Silica Resins for Direct and Efficient Extraction of DNA from Complex Biological Matrices in a Miniaturized Format" Analytical Biochemistry 283 (2000) pp. 175-191.
Cameron, et al. "High Internal Phase Emulsions (HIPEs) Structure, Properties and Use in Polymer Preparation" University of Strathclyde pp. 163-214.
He, et al. "Fabrication of Nanocolumns for Liquid Chromatography" Anal. Chem 1998 pp. 3790-3797.
Birnmoim, H.C. "A Rapid Alkaline Extraction Method for the Isolation of Plasmid DNA" Methods of Enzymology vol. 100 (1983) pp. 243-255.
McLaughlin, et al. "Molecular Approaches to the Identification of Streptococci" Methods in Molecular Medicine vol. 15 pp. 117-139.
Zhu, et al., "High-Sensitivity Capillary Electrophoresis of Double-Stranded DNA Fragments Using Monomeric and Dimeric Fluorescent Intercalating Dyes" Anal Chem 1994 pp. 1941-1948.
Medintz, et al. "Novel Energy Transfer Fluorescence Labeling Cassette" BioTechniques vol. 32 No. 2 (2002) p. 270.
Sun, et al. "A Heater-Integrated Transparent Microchannel Chip for Continuous Flow PCR" Sensors and Actuators B 84 (2002) pp. 283-289.
PCT International Search Report dated Aug. 26, 2004, Application No. PCT/US03/41466.
Canadian Office Action dated Jun. 10, 2011, Application No. 2,512,071.
Notification of Provisional Rejection mailed Oct. 21, 2011 for Application No. 2006-7026091.
Final Office Action mailed Sep. 12, 2011 from U.S. Appl. No. 12/844,544.
Final Office Action Final dated Jul. 8, 2011 issued in U.S. Appl. No. 11/978,224.
Chinese Office Action mailed Oct. 9, 2011, in Application No. 200910160476.0.
Chinese Notice of Amendment issued Aug. 30, 2011 for Appl. No. 201110197721.2.
Office Action Final dated Feb. 8, 2012 issued in U.S. Appl. No. 12/203,800.
Korean Office Action mailed Oct. 11, 2011, for Application No. 2011-7015771.
Office Action Final dated Feb. 24, 2012 issued in U.S. Appl. No. 12/819,094.
Office Action dated Apr. 12, 2012 issued in U.S. Appl. No. 13/372,376.
Notice of Allowance mailed Jun. 8, 2012 for U.S. Appl. No. 12/819,094.
Allowed Claims as of Jun. 8, 2012 for U.S. Appl. No. 12/819,094.
Office Action dated Jul. 6, 2012 issued in U.S. Appl. No. 12/670,377.
Final Office Action dated Jul. 13, 2012 issued in U.S. Appl. No. 12/203,800.
Japanese Office Action mailed Sep. 4, 2012 for Application No. 2011-155300.

(56) References Cited

OTHER PUBLICATIONS

Japanese Decision on Rejection mailed Apr. 3, 2012 for Application No. 2007-515379.
European Office Action mailed Oct. 23, 2012 from Application No. 05804847.1.
Japanese Decision of Rejection dated Mar. 15, 2011, from Application No. 2005-508628.
International Search Report mailed Oct. 10, 2008 issued in PCT/US2008/071086.
Notice of Allowance dated Dec. 10, 2012 issued in U.S. Appl. No. 13/372,376.
Office Action dated Nov. 4, 2013 issued in U.S. Appl. No. 11/978,224.
Amendment and Request for Correction of Inventorship mailed Jan. 10, 2008 U.S. Appl. No. 10/750,533.
Anderson, et al. A miniature integrated device for automated multistep genetic assays. Nucleic Acids Research. 2000;28:e60.
Bings, et al. Microfluidic Devices Connected to Fused-Silica Capillaries with Minimal Dead Dead Volume. Analytical Chemistry. 1999;71(15):3292-3296.
Blazej, et al. Microfabricated bioprocessor for integrated nanoliter-scale Sanger DNA sequencing. Proc. Natl. Acad. Sci. USA 2006;103:7240-7245.
Rlazej, et al. Polymorphism Ratio Sequencing: A New Approach for Single Nucleotide Polymorphism Discovery and Genotyping. Genome Research. 2003;13:287-293.
Brenner, et al. Gene expression analysis by massively parallel signature sequencing (MPSS) on microbead arrays. Nature Biotechnology. 2000;18(6):630-634.
Buchholz, et al. The use of light scattering for precise characterization of polymers for DNA sequencing by capillary electrophoresis. Electrophoresis. 2001;22:4118-4128.
CAPLUS abstract of Krokhin et al. Modified silica as a stationary phase for ion chromatography. Journal of Chromatography A. 1995;706:93-8.
Chan, et al. Microfabricated Polymer Devices for Automated Sample Delivery of Peptides for Analysis by Electrospray Ionization Tandem Mass Spectrometry. Analytical Chemistry. 1999;71(20):4437-4444.
Chiem, et al. Microchip systems for immunoassay: an integrated immunoreactor with electrophoretic separation for serum theophylline determination. Clinical Chemistry.1998;44(3):591-598.
Chiem, et al. Room temperature bonding of micromachined glass devices for capillary electrophoresis. Sensors and Actuators. 2000;B63(3):147-152.
Curcio, et al. Continuous Segmented-Flow Polymerase Chain Reaction for High-Throughput Miniaturized DNA Amplification. Analytical Chemistry. 2003;75(1):1-7.
Diehl, et al. BEAMing: single-molecule PCR on microparticles in water-in-oil emulsions. Nature Methods. 2006;3(7):551-9.
Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.
Doherty, et al. Sparsely cross-linked "nanogels" for microchannel DNA sequencing. Electrophoresis. 2003;24(24):4170-4180.
Dorfman, et al. Contamination-Free Continuous Flow Microfluidic Polymerase Chain Reaction for Quantitative and Clinical Applications. Analytical Chemistry. 2005;77(11):3700-3704.
Doyle, et al. Self-Assembled Magnetic Matrices for DNA Separation Chips. Science. 2000;295:2237.
Dressman, et al. Transforming single DNA molecules into fluorescent magnetic particles for detection and enumeration of genetic variations. Proc Natl Acad Sci USA. 2003;100(15):8817-8822.
Ewing, et al. Base-Calling of Automated Sequencer Traces Using Phred. I. Accuracy Assessment. Genome Research. 1998;8:175-185.
Ewing, et al. Base-Calling of Automated Sequencer Traces Using Phred. II. Error probabilities. Genome Research. 1998;8:186-194.
Figeys, et al. A Microfabricated Device for Rapid Protein Identification by Microelectrospray Ion Trap Mass Spectrometry. Analytical Chemistry. 1997;69(16):3153-3160.
Figeys, et al. An Integrated Microfluidics-Tandem Mass Spectrometry System for Automated Protein Analysis. Analytical Chemistry. 1998;70(18):3728-3734.
Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications In Mass Spectrometry. 1998;12:1435-1444.
Figeys, et al. Nanoflow Solvent Gradient Delivery from a Microfabricated Device for Protein Identifications by Electrospray Ionization Mass Spectrometry. Analytical Chemistry. 1998;70(18):3721-3727.
Francis, et al. Flow analysis based on a pulsed flow of solution: theory, instrumentation and applications. Talanta. 2002;58(6):1029-1042.
Ghadessy, et al. Directed evolution of polymerase function by compartmentalized self-replication. Proc Natl Acad Sci USA. 2001;98:4552-4557.
Giddings, et al. A software system for data analysis in automated DNA sequencing. Genome Research. 1998;8:644-665.
Goll, et al. Microvalves with bistable buckled polymer diaphragms. Journal of Micromechanics and Microengineering. 1996;6:77-79.
Grover, et al. Development and multiplexed control of latching pneumatic valves using microfluidic logical structures. Lab on a chip. 2006;6:623-631.
Grover, et al. An integrated microfluidic processor for single nucleotide polymorphism-based DNA computing. Lab on a Chip. 2005;5(10):1033-1040.
Grover, et al. Monolithic Membrane Valves and Diaphragm pumps for Practical Large-Scale Integration into Glass Microfluidic Devices. 2003;89:315-323.
Grover, et al. Practical Valves and Pumps for Large-Scale Integration into Microfludic Analysis Devices. Micro Total Analysis Systems. 2002;1:136-138.
Hansen, et al. A robust and scalable microfluidic metering method that allows protein crystal growth by free interface diffusion. Proc Natl Acad Sci USA. 2002;99(26):16531-16536.
Harrison, et al. Micromachining a Miniaturized Capillary Electrophoresis-Based Chemical Analysis System on a Chip. Science 1993;261; 895-897.
Hayes, et al. EDGE: A Centralized Resource for the Comparison, Analysis, and Distribution of Toxicogenomic Information. Molecular Pharmacology. 2005;67(4):1360-1368.
International Preliminary Report for corresponding PCT Application No. PCT/CA2000/01421 dated Feb. 14, 2002.
International Preliminary Report for corresponding PCT Application No. PCT/US2005/018678 dated Nov. 13, 2007.
International Preliminary Report for corresponding PCT Application No. PCT/US2005/033347 dated Mar. 20, 2007.
International Preliminary Report for corresponding PCT Application No. PCT/US2007/007381 dated Sep. 23, 2008.
International Preliminary Report for corresponding PCT Application No. PCT/US2007/02721 dated Aug. 5, 2008.
International Preliminary Report for corresponding PCT Application No. PCT/US2007/061573 dated Aug. 26, 2008.
International Search Report for PCT/US2005/033347.
Ju, et al. Fluorescence energy transfer dye-labeled primers for DNA sequencing and analysis. Proc. Natl. Acad. Sci. USA. 1995;92:4347-4351.
Kan, et al. A novel thermogelling matrix for micro channel DNA sequencing based on poly-N-alkoxyalkylaclylamide copolymers. Electrophoresis. 2003;24(24):4161-4169.
Koh, et al. Integrating Polymerase Chain Reaction, Valving, and Electrophoresis in a Plastic Device for Bacterial Detection. Analytical Chemistry. 2003;75(17):4591-4598.
Kopp, et al. Chemical Amplification Continuous-Flow PCR on a Chip. Science. 1998;280:1046-1048.
Lagally, et al. Fully integrated PCR-capillary electrophoresis microsystem for DNA analysis. Lab on a Chip. 2001;1(2):102-107.

(56) References Cited

OTHER PUBLICATIONS

Lagally, et al. Integrated Portable Genetic Analysis Microsystem for Pathogen/Infectious Disease Detection. Analytical Chemistry. 2004;76:3162-3170.
Lagally, et al. Monolithic integrated microfluidic DNA amplification and capillary electrophoresis analysis system. Sensors and Actuators. 2000;B63(3):138-146.
Lagally, et al. Single-Molecule DNA Amplification and Analysis in an Integrated Microfluidic Device. Analytical Chemistry. 2001;73(3): 565-570.
Lazar, et al. Subattomole-Sensitivity Microchip Nanoelectrospray Source with Time-of-Flight Mass Spectrometry Detection. Analytical Chemistry. 1999;71(17):3627-3631.
Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.
Li, et al. Rapid and sensitive separation of trace level protein digests using microfabricated devices coupled to a quadrupole-time-of-flight mass spectrometer. Electrophoresis. 2000;21:198-210.
Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.
Licklider, et al. A Micromachined Chip-Based Electrospray Source for Mass Spectrometry. Analytical Chemistry. 2000;72(2):367-375.
Lisec, et al. A bistable pneumatic microswitch for driving fluidic components. Sensors and Actuators. 1996;A54:746-749.
Liu, et al. Automated parallel DNA sequencing on multiple channel microchips. Proc. Natl. Acad. Sci. USA. 2000;97(10):5369-5374.
Liu, et al. Optimization of High-Speed DNA Sequencing on Microfabricated Capillary Electrophoresis Channels. Analytical Chemistry. 1999;71:566-573.
Margulies, et al. Genome sequencing in microfabricated high-density picolitre reactors. Nature. 2005;437(7057):376-80. (Abstact only).
Melin, et al. A Passive 2-Dimensional Liquid Sample Micromixer. 7th International Conference on Miniaturized Chemical and Biochemical Analysis Systems. 2003;167-170.
Mitra, et al. Digital genotyping and haplotyping with polymerase colonies. Proc Natl Acad Sci USA. 2003 . 100(10):15926-5931.
Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.
Ocvirk, et al. High Performance Liquid Chromatography Partially Integrated onto a Silicon Chip. Analytical Methods and Instrumentation. 1995;2:74-82.
Ocvirk, et al. Optimization of confocal epifluorescence microscopy for microchip-based miniaturized total analysis systems. The Analyst. 1998;123:1429-1434.
Office Action Final dated Feb. 19, 2008 issued in U.S. Appl. No. 10/540,658.
Office Action Final dated Feb. 6, 2008 issued in U.S. Appl. No. 11/139,018.
Office Action mailed Apr. 27, 2007 in U.S. Appl. No. 11/139,018, filed May 25, 2005.
Office Action mailed Jul. 2, 2007 in U.S. Appl. No. 10/540,658, filed Jun. 23, 2005.
Office Action mailed Jul. 12, 2007 in U.S. Appl. No. 10/750,533, filed Dec. 29, 2003.
Ohori, et al. Partly disposable three-way mirovalve for a medical micro total analysis system (muTAS). Sensors and Actuators. 1998;A64(1): 57-62.
Oleschuk, et al. Trapping of Bead-Based Reagents within Microfluidic Systems: On-Chip Solid-Phase Extraction and Electrochromatography. Analytical Chemistry. 2000;72:585-590.
Olsen, et al. Immobilization of DNA Hydrogel Plugs in Microfluidic Channels. Analytical Chemistry. 2002;74:1436-1441.
Paegel, et al. High-throughput DNA sequencing with a 96-lane capillary array electrophoresis bioprocessor. Proc Natl Acad Sci USA. 2002;99:574-579.
Paegel, et al. Microchip Bioprocessor for Integrated Nanovolume Sample Purification and DNA Sequencing. Analytical Chemistry. 2002;74(19):5092-5098.
Paegel, et al. Microfluidic devices for DNA sequencing: sample preparation and electrophoretic analysis. Current Opinion in Biotechnology. 2003;14(1):42-50.
Paegel, et al. Turn Geometry for Minimizing Band Broadening in Microfabricated Capillary Electrophoresis Channels. Analytical Chemistry. 2000;72:3030-3037.
PCT Notification of Transmittal of the International Search Report and The Written Opinion of the International Searching Authority, or the Declaration, mailed Jun. 17, 2008, Application No. PCT/US2007/082568.
Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.
Ramsey, et al. Generating Electrospray from Microchip Devices Using Electroosmotic Pumping. Analytical Chemistry. 1997;69(6):1174-1178.
Rohr, et al. Porous polymer monoliths: Simple and efficient mixers prepared by direct polymerization in the channels of microfluidic chips. Electrophoresis. 2001;22:3959-3967.
Rye, et al. High-sensitivity two-color detection of double-stranded DNA with a confocal fluorescence gel scanner using ethidium homodimer and ihiazole orange. Nucleic Acids Research. 1991;19(2):327-333.
Scherer, et al. High-Pressure Gel Loader for Capillary Array Electrophoresis Microchannel Plates. Biotechniques. 2001;31(5):1150-1154.
Schomburg, et al. Design Optimization of Bistable Microdiaphragm Valves. Sensors and Actuators. 1998;A64:259-264.
Seifar, et al. Capillary electrochromatography with 1.8-mum ODS-modified porous silica particles. Journal of Chromatography. 1998; A808:71-77.
Simpson, et al. High-throughput genetic analysis using microfabricated 96-sample capillary array electrophoresis microplates. Proc Natl Acad Sci USA. 1998;95:2256-2261.
Simpson, et al. Microfabrication Technology for the Production of Capillary Array Electrophoresis Chips. Biomedical Microdevices. 1998;1:7-26.
Soper, et al. Sanger DNA Sequencing Reactions Performed in a Solid-Phase Nanoreactor Directly Coupled to Capillary Gel Electrophoresis. Analytical Chemistry. 1998;70:4036-4043.
Spiering, et al. Novel microstructures and technologies applied in chemical analysis techniques. 1997 International Conference on Solid-State Sensors and Actuators. 1997;1:511-514.
Takao, et al. A Pneumatically Actuated Full In-Channel Microvalve With MOSFET-Like Function in Fluid Channel Networks. Journal of Microelectromechanical Systems. 2002;11(5):421-426.
Takao, et al. Microfluidic Integrated Circuits for Signal Processing Using Analogous Relationship Betweeen Pneumatic Microvalve and MOSFET. Journal of Microelectromechanical Systems. 2003;12(4):497-505.
Thomas, et al. Application of Genomics to Toxicology Research. Environmental Health Perspectives. 2002;110(6):919-923.
Tice, et al. Formation of Droplets and Mixing in Multiphase Microfluidics at Low Values of the Reynolds and the Capillary Numbers. Langmuir. 2003;19:9127-9133.
Unger, et al. Monolithic Microfabricated Valves and Pumps by Multilayer Soft Lithography. Science. 2000;288:113-116.
Van Der Moolen, et al. A Micromachined Injection Device for CZE: Application to Correlation CZE. Analytical Chemistry. 1997;69(20):4220-4225.
Van Der Moolen, et al. Correlation Capillary Zone Electrophoresis, a Novel Technique to Decrease Detection Limits. Chromatographia. 1995;40(7/8):368-374.
Vazquez, et al. Electrophoretic Injection within Microdevices. Analytical Chemistry. 2002;74:1952-1961.

(56) References Cited

OTHER PUBLICATIONS

Veenstra, et al. The design of an in-plane compliance structure for microfluidical systems. Sensors and Actuators. 2002;B81:377-383.
Waller, et al. Quantitative Immunocapture PCR Assay for Detection of Campylobacter jejuni in Foods. Applied Environmental Microbiology. 2000.
Weimer, et al. Solid-Phase Capture of Proteins, Spores, and Bacteria. Applied Environmental Microbiology. 2001;67(3):1300-1307.
Wen, et al. Microfabricated isoelectric focusing device for direct electrospray ionization-mass spectrometry. Electrophoresis. 2000;21:191-197.
Wikipedia brochure for defining stocahstic process. Sep. 2, 2009.
Williams, et al. Amplification of complex gene libraries by emulsion PCR. Nature Methods. 2006;3(7):545-50.
Woolley, et al. Functional Integration of PCR Amplification and Capillary Electrophoresis in a Microfabricated DNA Analysis Device. Analytical Chemistry. 1996;68(23):4081-4086.
Wright, et al. Behavior and Use of Nonaqueous Media without Supporting Electrolyte in Capillary Electrophoresis and Capillary Electrochromatography. Analytical Chemistry. 1997;69(16):3251-3259.
Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.
Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.
Xue, et al. Multichannel Microchip Electrospray Mass Spectrometry. Analytical Chemistry. 1997;69(3):426-430.
Yang, et al. A MEMS thermopneumatic silicone rubber membrane valve. Sensors and Actuators. 1998;A64(1):101-108.
Yu, et al. Preparation of Monolithic Polymers with Controlled Porous Properties for Microfluidic Chip Applications Using Photoinitiated Free Radial Polymerization. Journal of Polymer Science. 2002;40:755-769.
Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.
Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.
Zhang, et al. Microfabricated Devices for Capillary Electrophoresis-Electrospray Mass Spectrometry. Analytical Chemistry. 1999;71(15):3258-3264.
Chinese Office Action dated Jan. 25, 2008, from Application No. 2003801100666.
Hultman, T.S., et al. Bidirectional Solid-Phase Sequenceing of in Vitro-Amplified Plasmid DNA. Bio Techniques, 1991. 10:p. 84-93.
Nakano, H., et al., "Single-Step Single-Molecule PCR of DNA with a Homo-Priming Sequence Using a Single Primer and Hot-Startable DNA Polymerasem," Journal of Bioscience and Bioengineering, 2000, vol. 90:4, pp. 456-458.
Leamon, J.H., et al., A massively parallel Pico Titer Plate (TM) based platform for discrete picoliter-scale polymerase chain reactions, Electrophoresis, 2003, vol. 24, pp. 3769-3777.
Ghadessy, F.J., et al., "Directed evolution of polymerase function by compartmentalized self-replication," PNAS, 2001, vol. 98, pp. 4552-4557.
Fleming, et al., "LD-PCR coupled to long-read direct sequencing: an approach for mutation detection in genes with compact genomic structures," Journal of Biochemical and Biophysical Methods, 2001, vol. 47:1-2, pp. 131-136.
Kamei, T., et al., "Integrated Hydrogenated Amorphous Si Photodiode Detector for Microfluidic Bioanalytical Devices," Analytical Chemistry, 2003, vol. 75, pp. 5300-5305.
Albarghouthi, M.N., "Poly-N-hydroxyethylacrylamide (polyDuramide): A novel hydrophilic self-coating polymer matrix for DNA sequencing by capillary electrophroesis," Electrophoresis, 2002. vol. 23, pp. 1429-1440.
Song, H., et al., "A microfluidic system for controlling reaction networks in time," Angewandte Chemie-International Edition 42, 2003. pp. 768-772.
Srinivasan, U., et al., "Alkyltrichlorosilane-based self-assembled monolayer films for stiction reduction in silicon micromachines," Journal of Microelectromechanical Systems, 1998, vol. 7, pp. 252-260.
Thorsen et al., "Microfludic Large-Scale Integration", Science, vol. 298, Oct. 18, 2002, pp. 580-584.
Park, Nokyoung, et al., "Cylindrical Compact Thermal-Cycling Device For Continuous-Flow Polymerase Chain Reaction," Anal. Chem., Nov. 1, 2003, vol. 75, No. 21, pp. 6029-6033.
Emrich et al., "Microfabricated 384-lane capillary array electrophoresis bioanalyzer for ultrahigh-throughput genetic analysis," Analytical Chemistry, 2002, vol. 74:19, pp. 5076-5083.
Mathies, R.A., et al., "Capillary array electrophoresis bioprocessors, Solid-State Sensor," Actuator and Microsystems Workshop, 2002, pp. 112-117, Hilton Head Island, SC, USA.
Ligler, F.S., et al., "Integrating Waveguide Biosensor," Anal. Chem., 2002, vol. 74, pp. 713-719.
Notice of Allowance and Fees Due mailed Aug. 13, 2008 from U.S. Appl. No. 10/750,533.
Allowed Claims from U.S. Appl. No. 10/750,533.
Office Action dated Oct. 8, 2008 issued in U.S. Appl. No. 10/540,658.
Office Action Final dated Mar. 2, 2009 issued in U.S. Appl. No. 10/540,658.
International Search Report and The Written Opinion of the International Searching Report Oct. 29, 2007, Application No. PCT/US2005/018678.
Mathies, et al., U.S. Appl. No. 10/750,533, titled "Fluid Control Structures in Microfluidic Devices," filed Dec. 29, 2003.
Mathies, et al., U.S. Appl. No. 12/203,800, titled "Fluid Control Structures in Microfluidic Devices," filed Sep. 3, 2008.
Mathies, et al., U.S. Appl. No. 10/540,658, titled "Methods and Apparatus for Pathogen Detection and Analysis," filed Jun. 23, 2005.
Mathies, et al., U.S. Appl. No. 11/139,018, titled "Microfabricated Integrated DNA Analysis System," filed May 25, 2005.
Mathies, et al., U.S. Appl. No. 11/726,701, titled "Multiplexed Latching Valves for Microfluidic Devices and Processors," filed Mar. 21, 2007.
Office Action Final dated Aug. 27, 2008 issued in U.S. Appl. No. 11/139,018.
Office Action Final dated Apr. 29, 2009 issued in U.S. Appl. No. 11/139,018.
PCT Notification of Transmittal of the International Search Report and The Written Opinion of the International Searching Authority, or the Declaration, mailed Jul. 15, 2008, Application No. PCT/US2007/007381.
Htdekunt, T., et al. Pneumatically Actuated Full In Channel Microvalve With MOSFET-Like Function IN Fluid Channel Networks, Journal of Microelectromechanical Systems, 2002, 11:5; 421-426. P066).
Hidekuni, T., et al., Microfluidic Integrated Circuits for Signal Processing Using Analogous Relationship Between Pneumatic Microvalve and MOSFET, Journal of Microelectromechanical System 2003, 12:4; 497-505.
Mircea, C., et al., Design Fabrication and Testing of a Bistable Electromagnetically Actuated Microvalve. Journal of Microeclectromechanical System 2000. vol. 9; 181-189.
Press, W., et al., An Integrated Microfluidic Processor for Single Nucleotide Polymorphism-based DNA Computing, Lab On A Chip. 2005, 5:10, 8 pages.
Roth, C. et al., Fundamentals of Logic Design, $3^{rd}$ Edition, West Publishing Company, 1985 (Table of Content).
Press, W., et al., The Art of Scientific Computing, Numerical Recipes In C, 2nd Edition, Cambridge University Press, 1992, (table of Contents).

(56) References Cited

OTHER PUBLICATIONS

Office Action Final dated Dec. 11, 2009 issued in U.S. Appl. No. 11/726,701.
Office Action Final dated Nov. 6, 2009 issued in U.S. Appl. No. 11/139,018.
Office Action Final dated Feb. 22, 2010 issued in U.S. Appl. No. 11/139,018.
Notice of Allowance for U.S. Appl. No. 11/139,018 mailed Jul. 1, 2010.
Allowed Claims for U.S. Appl. No. 11/139,018.
Mathies, et al., U.S. Appl. No. 12/782,598, titled "Fluid Control Structures in Microfluidic Devices," filed May 18, 2010,
Chinese Office Action Final dated Feb. 24, 2010 issued Appl. No. 200780018073.1.
Notice of Allowance and Fees Due mailed May 6, 2010 from U.S. Appl. No. 11/726,701.
Allowed Claims from U.S. Appl. No. 11/726,701.
Blazej, et al., Inline Injection Microdevice for Attomole-Scale Sanger DNA Sequencing, *Anal. Chem.*, 2007, 79(12), pp. 4499-2506.
Mathies, et al., U.S. Appl. No. 12/844,544, titled "Microfabricated Integrated DNA Analysis System," filed Jul. 27, 2010.
Japanese Office Action dated Jan. 13, 2010, from Application No. 2005-508628.
Japanese Office Action dated Aug. 10, 2010, from Application No. 2005-508628.
European Supplemental Search Report dated Sep. 1, 2010 from Application No. 05804847.1
Hjerten, High-Performance Electrophoresis: Elimination of Electronendosmosis and Solute Adsorption, J. Chromotography, 347, 1985, pp. 191-198.
Office Action Final dated Jan. 20, 2010 issued in U.S. Appl. No. 11/978,224.
Mathies, et al., U.S. Appl. No. 12/782,598, titled "Fluid Control Structures in Microfluidic Devices," filed May 18, 2010.
Mathies, et al., U.S. Appl. No. 11/978,224, titled "Inline-Injection Microdevice and Microfabricated Integrated DNA Analysis System Using Same," filed Oct. 25, 2007.
Office Action dated Oct. 25, 2010 issued in U.S. Appl. No. 11/978,224.
Hartmann, A., et al., "Direct immobilization of Antibodies on Phthalocyaninato-polysiloxane Photopolymers," Thin Solid Films, 245, 1994, pp. 206-210.
Hartmann, A., et al., One-Step Immobilization of Immunoglobulin G and Potential of the Method for Application in Immunosensors, Sensors and Actuators 28 (2), 1995, pp. 143-149.
Sanford, et al., "Photoactivatable Cross-Linked Polyacrylamide for the Site-Selective Immobilization of Antigens and Antibodies," Chem Mater., 1998, vol. 10, No. 6, pp. 1510-1520.
Japanese Second Office Action, mailed Aug. 2010, Application No. 2005-508628.
Office Action mailed Jan. 7, 2011 from U.S. Appl. No. 12/844,544.
Notification of Provisional Rejection mailed Jan. 17, 2011, in Application No. 2005-7012095.
Yu, Cong, et al., "Towards Stationary Phases for Chromatography on a Microchip: Molded Porous Polymer Monoliths Prepared in Capillaries By Photoinitiated in situ Polymerization as Separation Media for Electrochromatography," Electrophoresis 2000, vol. 21, pp. 120-127.
Request for Ex Parte Reexamination of U.S. Pat. No. 7,445,926.
Hosokawa, et al., "A Pneumatically-Actuated Three-Way Microvalve Fabricated with Polydimcthylsiloxanc Using the Mcmbranc Transfcr Tcchniquc," J. Micrmcch. Microeng., vol. 10, 2000, pp. 415-420.
Office Action dated Feb. 27, 2014 issued in U.S. Appl. No. 12/203,800.
Notice of Allowance dated Feb. 1, 2013 issued in U.S. Appl. No. 12/670,377.
Notice of Allowance dated Jun. 10, 2014 issued in U.S. Appl. No. 11/978,224.
EP Office Action dated Sep. 6, 2013 issued in Application No. 11184291.0.
EP Extended Search Report dated Nov. 29, 2011, issued in Application No. 11184291.0.
Office Action dated Jul. 14, 2015, issued in U.S. Appl. No. 12/203,800.
Office Action dated Aug. 24, 2016, issued in U.S. Appl. No. 12/203,800.

\* cited by examiner

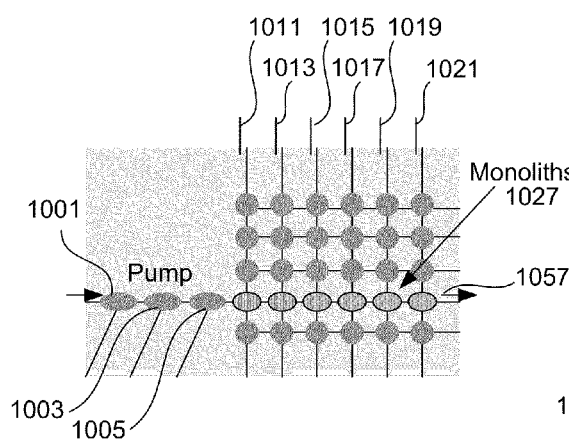 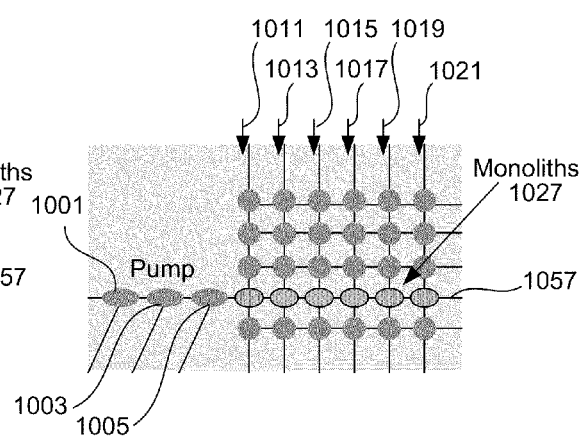
FIG. 10A  FIG. 10B

FLUID CONTROL STRUCTURES IN MICROFLUIDIC DEVICES

CROSS REFERENCE TO RELATED APPLICATIONS

This application is a divisional of and claims priority to U.S. application Ser. No. 12/203,800 filed Sep. 3, 2008, titled, "Fluid Control Structures in Microfluidic Devices," which is a divisional of and claims priority to U.S. application Ser. No. 10/750,533, filed Dec. 29, 2003, now U.S. Pat. No. 7,445,926, issued Nov. 4, 2008, titled "Fluid Control Structures in Microfluidic Devices," which claims benefit from U.S. Provisional Patent Application No. 60/475,013 filed May 30, 2003, titled "Monolithic Membrane Structures for Fluid Control in Glass Microfluidic Devices", and from U.S. Provisional Patent Application No. 60/437,262 filed Dec. 30, 2002, titled "Microfabricated Immuno-Genetic Pathogen Analyzer," the entireties of which are incorporated by reference for all purposes.

Statement Regarding Federally Sponsored Research

This invention was made with government support under contract numbers DE-FG03-91ER61125 awarded by the U.S. Department of Energy and NAG5-9659 awarded by the National Aeronautics and Space Administration, and by grant numbers HG001399 and P01 CA077664 awarded by the National Institutes of Health. The government has certain rights in the invention.

BACKGROUND OF THE INVENTION

The present invention relates to microfluidic devices. In one example, the present invention provides microfluidic control structures for effectively implementing sample preparation, processing, detection and analysis systems.

Conventional mechanisms for microfluidic analysis are limited. Some available mechanisms include single channel separation devices and multiple channel separation devices. Others include analyzers that integrate some sample preparation and analysis steps. However, many microfluidic analysis devices that include fluidic control capabilities are chemically or physically incompatible with many chemical or biochemical assays. In addition, many microfluidic control elements are difficult to fabricate in dense arrays because of limitations in the fabrication process, robustness, and/or design. Many conventional devices require constant actuation to maintain fluidic control. A microfluidic device utilizing such valves can not be removed from its control system without losing control of the fluidic contents of the device. In addition, many techniques and mechanisms for microfluidic analysis furthermore lack sensitivitity, specificity, or quantitative analysis capabilities. In particular, conventional microfluidic analysis mechanisms lack the functionality and capabilities to efficiently implement sample preparation for systems such as pathogen detectors and analyzers.

It is therefore desirable to provide improved methods and apparatus for implementing microfluidic control mechanisms such as valves, pumps, routers, reactors, etc. to allow effective integration of sample introduction, preparation processing, and analysis capabilities in a microfluidic device. In one example, it is desirable to provide microfluidic devices having microfabrication efficiencies that can be used to implement both single channel and array based systems that can be used as pathogen detectors and analyzers that provide few false positives, high throughput and inexpensive continuous monitoring.

SUMMARY OF THE INVENTION

Methods and apparatus for implementing microfluidic analysis devices are provided. A monolithic elastomer membrane associated with an integrated pneumatic manifold allows the placement and actuation of a variety of fluid control structures, such as structures for pumping, isolating, mixing, routing, merging, splitting, preparing, and storing volumes of fluid. The fluid control structures can be used to implement a variety of sample introduction, preparation, processing, and storage techniques.

In one embodiment, a microfluidic structure is provided. The microfluidic structure includes a first surface, a second surface, and an elastomer membrane. The first surface includes a pneumatic channel. The second surface includes a fluidic channel. An elastomer membrane is located between the first and second surfaces such that the application of a pressure or a vacuum to the pneumatic channel causes the membrane to deflect to modulate a flow of a fluid in the fluidic channel.

In another embodiment, a microfluidic structure is provided. A first layer includes a pneumatic channel. A second layer includes a plurality of vias. A third layer includes a fluidic channel. An elastomer membrane is located between the first and second layers such that the application of a vacuum to the pneumatic channel causes the membrane to deflect to modulate a flow of a fluid in the fluidic channel.

In another embodiment, a microfluidic device is provided. The microfluidic devices includes a chemically compatible layer and a membrane layer. The chemically compatible layer has a plurality of channels. The channels are operable to provide paths for fluid flow. A membrane layer is coupled to the chemically compatible layer. Applying pneumatic pressure to regions of the membrane layer is operable to actuate a plurality of pneumatically switchable valves, wherein the pneumatically switchable valves are operable to control fluid flow on the microfluidic device.

In yet another embodiment, a method for controlling fluid flow on a microfluidic device is provided. An input valve is opened and an output valve is closed by varying pneumatic pressure to one or more regions of a membrane layer coupled to a glass layer. The glass layer includes a plurality of etched channels. The etched channels are operable to provide paths for fluid flow. A diaphragm valve is opened and the input valve is closed by varying pneumatic pressure. The output valve is opened and the diaphragm valve is closed. Closing the diaphragm valve pumps analyte fluid through the open output valve.

These and other features and advantages of the present invention will be presented in more detail in the following specification of the invention and the accompanying figures, which illustrate by way of example the principles of the invention.

BRIEF DESCRIPTION OF THE DRAWINGS

The invention may best be understood by reference to the following description taken in conjunction with the accompanying drawings, that illustrate specific embodiments of the present invention.

FIGS. 10A and 10B are diagrammatic representations showing capture and routing of analytes for immunoaffinity capture.

DETAILED DESCRIPTION OF SPECIFIC EMBODIMENTS

Figure 1A:
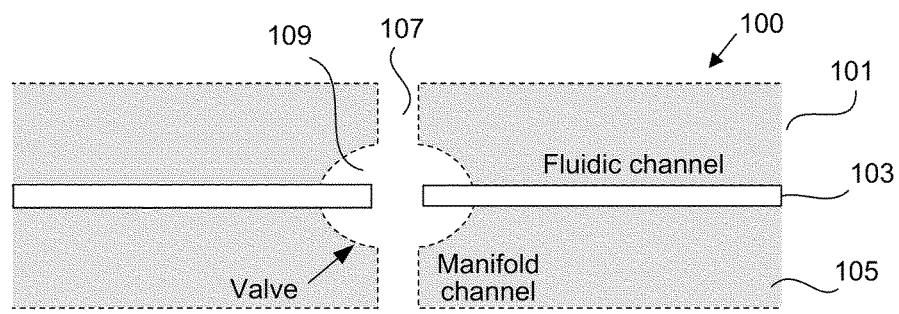
FIGS. 1A-1E are diagrammatic representations showing mechanisms on a microfluidic device suitable for implementing the techniques of the present invention.

Reference will now be made in detail to some specific embodiments of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. For example, the techniques of the present invention will be described in the context of glass microfluidic devices, although other devices such as plastic devices could also be used.

It should be noted that the fluid control structures suitable for use in glass microfluidic devices can be applied to a variety of microfluidic devices. A pathogen detection system is a good example of one possible application that can benefit from the use of fluid control structures. In the following description, numerous specific details are set forth in order to provide a thorough understanding of the present invention. The present invention may be practiced without some or all of these specific details. In other instances, well known process operations have not been described in detail in order not to unnecessarily obscure the present invention.

The field of microfluidic analysis technology has evolved rapidly from the earliest single channel separation devices. Some devices include multichannel separation devices for high throughput analysis and analyzers that integrate sine sample preparation and analysis on a single chip. Devices that combine both multichannel analysis and integrated sample preparation are capable of reducing the amount of resources and cost needed to perform a variety of assays. An illustrative example may be found in the field of genomics: integration of sequencing sample preparation, purification, and electrophoretic analysis in a single device translates into decreases in assay time and cost and increased assay throughput efficiency and robustness. In all cases, a high level of integration in a microfluidic device requires a robust on chip mechanism for isolating, routing, merging, splitting, and storing volumes of fluid.

Some valve technologies for use in silicon, glass silicon, polymer, and elastomer microfluidic devices have addressed these requirements in a limited manner. However, many of these technologies are chemically or physically incompatible with many chemical or biochemical assays. Furthermore, many technologies lack the variety of robust surface modification chemistries available for glass microfluidic devices. In addition, individual microfluidic valves are typically fabricated with separate membranes normally held open. Having valves normally open requires constant actuation to maintain fluidic control. A microfluidic device utilizing such valves cannot be removed from a control system without losing control of the fluidic contents of the device. Furthermore, some typical devices use individually placed latex membranes. Individually placed pneumatically actuated latex membranes haven been developed but this fabrication method prevents large scale integration into multichannel, high throughput analysis devices.

Other microfluidic devices are fabricated using anodically bonded silicon and glass wafers and actuated piezoelectrically. However, the electrical conductivity and chemical compatibility of silicon complicates use in analytical devices. Thin films bonded to or deposited on silicon can only partially mitigate the electrical conductivity and chemical compatibility.

Elastomer devices have also been demonstrated. However, the hydrophobicity and porosity of elastomeric materials render elastomeric devices incompatible with many chemical and biochemical assays. It is thus desirable to minimize the fluidic contact with elastomer surfaces. Complex fabrication, chemical compatibility, unreliable fluid manipulation and other problems have made existing fluidic manipulation technologies inadequate for integration into large-scale, high-throughput lab-on-a-chip devices.

Consequently, the techniques and mechanisms of the present invention provide a monolithic membrane valve structure suitable for high density integration into microfluidic devices. A variety of fluid control structures based on the monolithic membrane valve structures are also provided.

A microfluidic device having a monolithic membrane is one example of a particularly suitable device for implementing a pathogen detection system on a chip. According to various embodiments, the pathogen detection system includes immunocapture and DNA analysis mechanisms such as polymerase chain reaction (PCR), and capillary electrophoresis (CE) mechanisms. In one example, the pathogen detection system can be implemented on a glass microfluidic device having a variety of fluidic control structures.

Figure 1B:
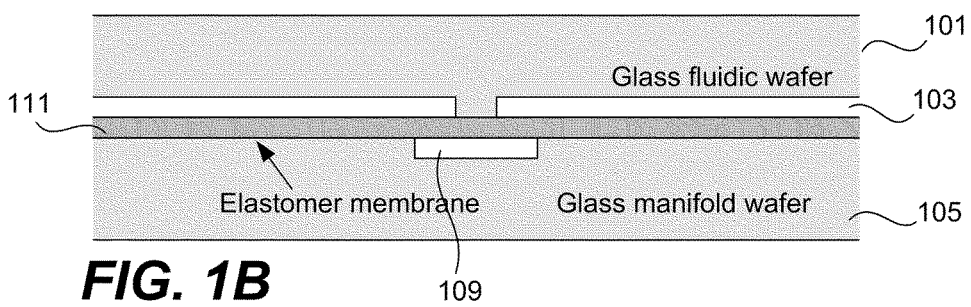
Figure 1C:
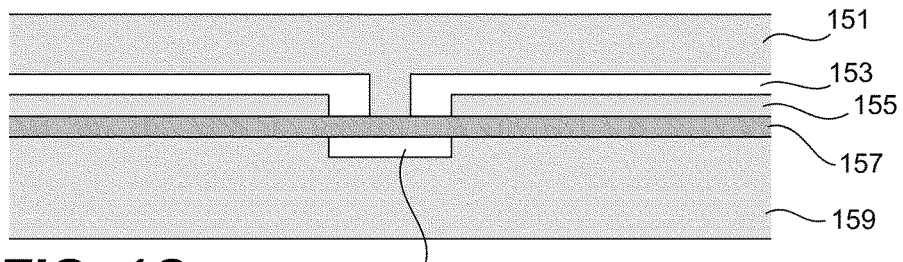
Figure 1D:
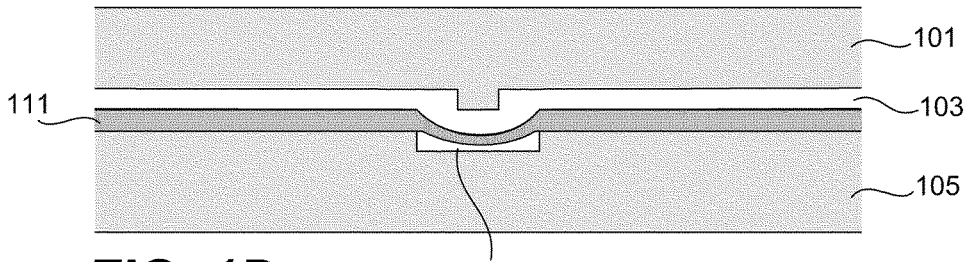
Figure 1E:
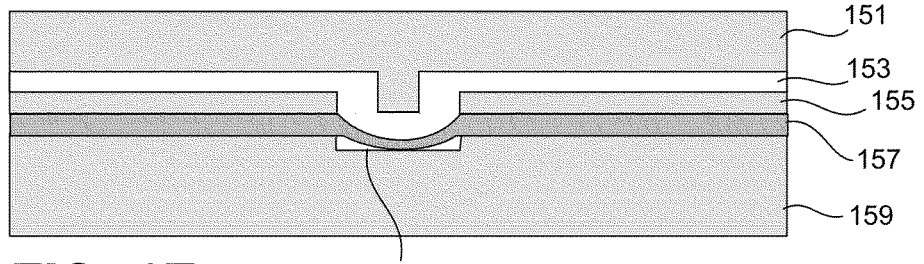

FIGS. 1A-1E are diagrammatic representations of monolithic membrane valves that can be implemented on a glass microfluidic device. FIG. 1A is a top view of a diagrammatic representation of a monolithic membrane valve. FIG. 1B is a side view of a diagrammatic representation of a three-layer device having the valve. FIG. 1C is a side view of a diagrammatic representation of a four-layer devices having the valve. FIG. 1D is a side view of a diagrammatic representation of an open valve of a three-layer device. FIG. 1E is a side view of aidagrammatic representation of an open valve four-layer device. According to various embodiments shown in FIGS. 1A and 1B, a three-layer glass microfluidic device includes an elastomer membrane 111 sandwiched between two glass wafers 101 and 105. In one example, the elastomer membrane is a polydimethysiloxane (PDMS) membrane available as 254 um thick HT-6135 and HT-6240 membranes from Bisco Silicons of Elk Grove, Ill. Other flexible membranes can also be used. The elastomer membrane 111 makes a reversible but strong bond between the wafers.

A fluidic channel 103 is etched in the wafers prior to bonding and is used to carry fluids. A manifold channel 107 and a valve area 109 are similarly etched to carry air or other working fluid under pressure or vacuum to actuate the valves. Typically, the pneumatic channels 107 and 109 are located on one wafer 105, herein referred to as the pneumatic wafer, and the fluidic channels are etched on the second wafer 101, herein referred to as the fluidic wafer. These etched channel features can directly contact the membrane and form a hybrid glass/elastomer channel as shown in FIG. 1B.

Alternatively, the membrane can be between a thermally bonded all-glass fluidic wafer sandwich (XY) and the pneumatic wafer 159 as shown in the four-layer device 150 of FIG. 1C. Having an all glass channel allows a device to benefit from the favorable physical and chemical properties of glass. Any layer having favorable physical and chemical properties is referred to as a chemically inactive layer. The chemically inactive layer can be used to fabricated XY. In one example, the sandwich of 151 and 155 that constitutes XY is made of glass.

An example of a four layer devices includes a fluidic wafer 151 thermally bonded to a via wafer 155. Via holes with small diameters are placed at the discontinuity in the fluidic channel 153. The elastomer membrane 157 is affixed to the via wafer 155 side of the fluidic/via wafer sandwich XZ. Valve deflection chambers 161 are etched in the manifold wafer 159 and bonded to the membrane 157, completing the 4-layer device 150. In this way, fluidic channel 153 retain san all-glass chemically favorable configuration while allowing implementation of the large-scale integrated fluidic control structures. In some embodiments, the four layer device shown in FIG. 1C provides substantial benefits over a three layer device as it minimizes contact between a sample and an elastomer membrane.

According to various embodiments, the various fluid control components within the monolithic membrane device are actuated by applying pressure or vacuum to holes on the pneumatic wafer. Any single membrane is referred to herein as a monolithic membrane. Any single device with a monolithic membrane is referred to herein as a monolithic device. Mechanisms for supplying pressure or vacuum to etched channels associated with a pneumatic wafer are herein referred to as ports or pneumatic ports. In a three layer device, etched channels in the pneumatic wafer distribute the actuation vacuum to valve region 109 of the elastomer membrane 111. Vacuum applied via the manifold channel at valve area region 109 deflects the membrane away from the channel discontinuity, providing a path for fluid flow across the discontinuity and thus opening the valve as shown in FIG. 1D. Valves that can be opened or closed using pneumatic pressure are herein referred to as switchable valves or pneumatically switchable valves.

Applying pneumatic pressure includes either applying pressure or applying a vacuum. The membrane 157 consequently can modulate the flow of fluid in the adjacent fluid channel as shown in FIG. 1D. In FIG. 1D, a vacuum is applied to valve area 109 through etched channels associated with pneumatic wafer 105 to open fluidic channel 103. When vacuum pressure or suction is no longer applied to valve area 109, the membrane 111 closes the fluidic channel 103 as shown in FIG. 1B. FIG. 1E shows a four layer device. The four layer device includes a channel layer 151, channel 153, via layer 155, membrane layer 157, and pneumatic layer 159. As noted above, the four layer device provides substantial benefits over a three layer device as it minimizes contact between a sample and an elastomer membrane in some cases to only a valve area 161.

It should be noted that the structures shown can be oriented in any direction. In some examples, valves can be inverted on a device. A pneumatic layer can be above or below a fluidic layer. The techniques of the present invention allow a variety of orientations, as gravity does not adversely affect the membrane valves.

The fluidic control structures provide a variety of benefits. For example, the monolithic membrane valves are normally closed valves, meaning that the valves remain closed even when the device is disconnected from the actuation pressure source. Existing normally open microfluidic valves require constant actuation to maintain control of the fluidic contents of the device. Furthermore, unlike shape memory alloy structures, both the closed and open temperatures of the valve structures are at ambient temperature, facilitating work with aqueous biological fluids.

In many typical implementations, a number of interfaces between the microfluidic device are needed in order to manipulate various fluidic control mechanisms. However, according to various embodiments of the present invention, multiple regions of a membrane can be actuated in parallel by connecting their pneumatic control channels. In one example, a series of valves can be controlled using a single pneumatic port. Consequently, a significant number of valves can be controlled using only a limited number of external interfaces or pneumatic ports. This simplifies implementation and minimizes problems interfacing with the device. According to various embodiments, controlling valves in this manner allows massively parallel pneumatic actuation of a monolithic membrane for operating valves, pumps, reservoirs, routers, and other fluid control structures within the device.

Figure 2A:
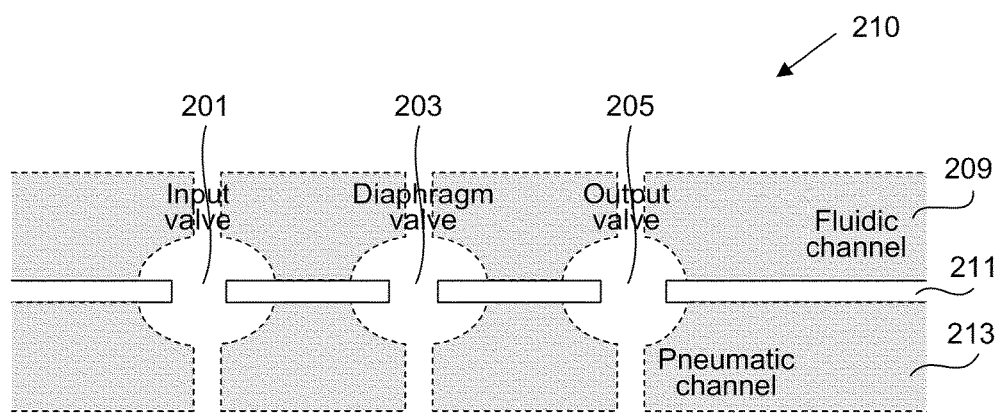
FIG. 2 is a diagrammatic representation depicting a diaphragm pump.
Figure 2B:
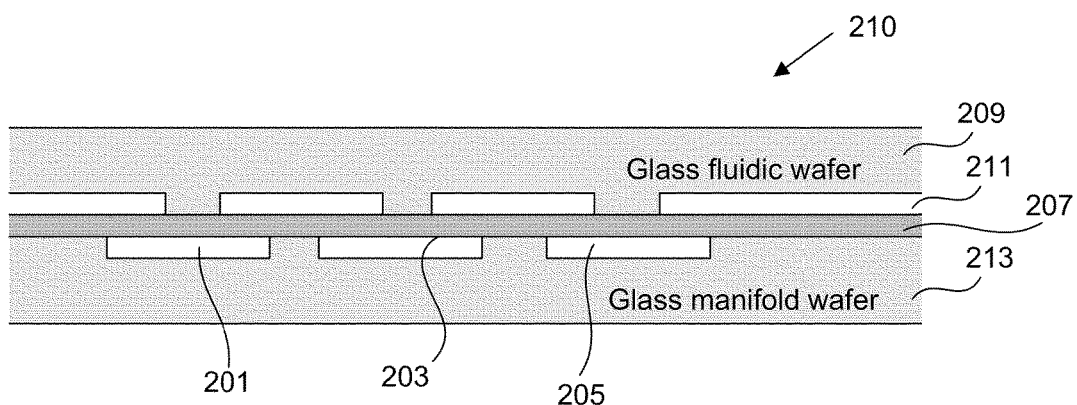

The membrane valves can be used to form a variety of fluidic control mechanisms. FIGS. 2A and 2B are diagrammatic representations of a pump formed using membrane valves. According to various embodiments shown in FIGS. 2A and 2B, three valves placed in series form a diaphragm pump 210. Pumping is achieved by actuating the valves according to a five step cycle. FIG. 2A shows a top view of a three-layer monolithic membrane diaphragm pump. FIG. 2B shows a side view of the three-layer monolithic membrane diaphragm pump. The diaphragm pump includes an input valve 201, a diaphragm valve 203, and an output valve 205. It should be noted that the diaphragm pump can operate in either direction and the designations of the input valve and output valve are arbitrary. The pump includes a fluidic layer 209 having etched fluidic channels 211, a monolithic membrane 207, and a manifold layer 213. The air tight nature of the valves makes the pumps self-priming and capable of pumping air in addition to other gases and fluids.

According to various embodiments, pumping can be performed in a series of stages. In a first stage, output valve 205 is closed and an input valve 201 is opened. In a second stage, a diaphragm valve 203 is opened. In a third stage, the input valve 201 is closed. In a fourth stage, the output valve 205 is opened. In a fifth stage, the diaphragm valve 203 is closed, pumping analyte fluid through the open output valve 205.

The volume pumped per cycle is determined by the volume contained within the open diaphragm valve, a volume that, in turn, determined by the size of the pneumatic chamber in the diaphragm valve. Therefore, pumps designed for metering known nanoliter to microliter scale volumes of fluid can be fabricated by modulating the size of the diaphragm valve pneumatic chamber. The diaphragm pumps are self-priming and can pump fluids forward or backward by reversing the actuation cycle. It should also be noted that the valve seat where the membrane contacts the glass sealing surface may be etched to have ridges or other surface modifications to control the adhesion of the membrane to the glass surface.

Figure 3:
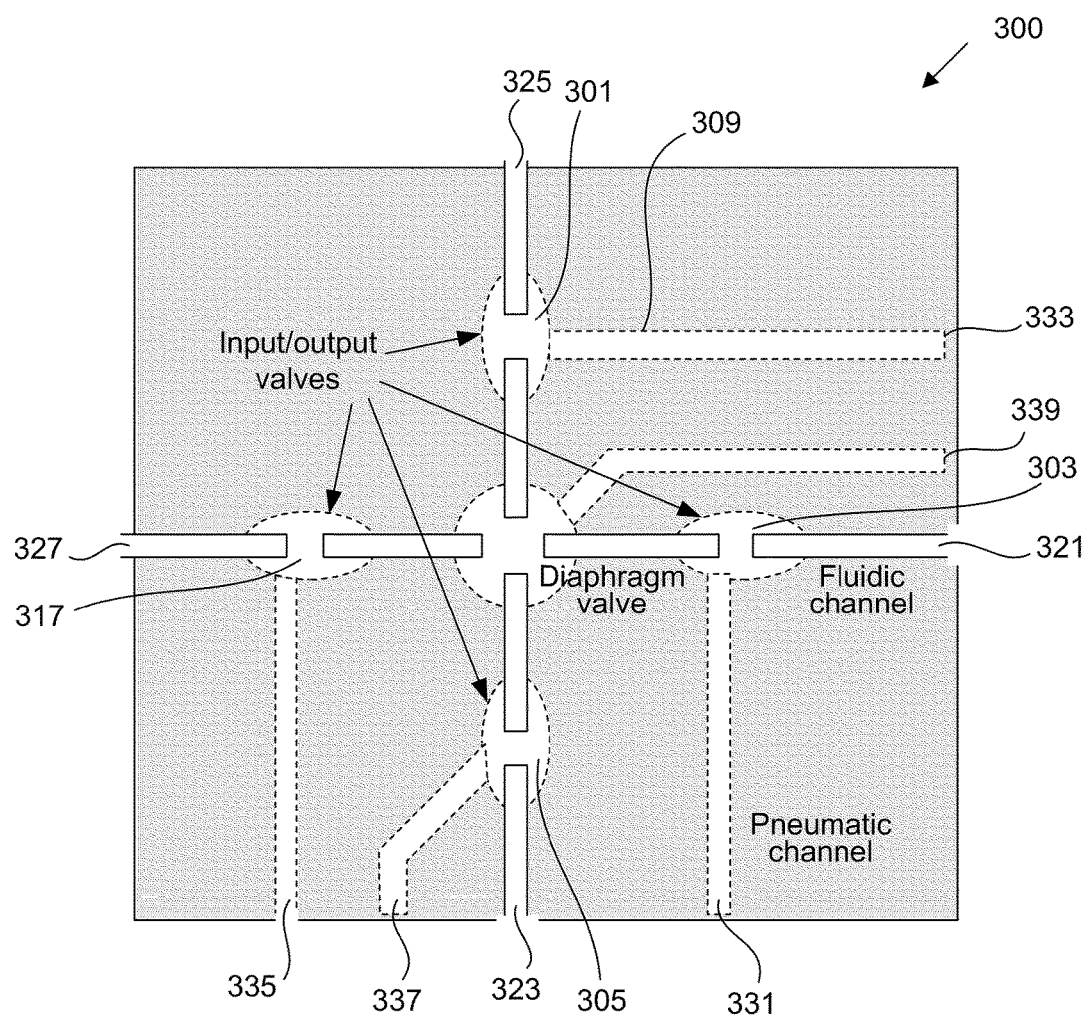
FIG. 3 is a plan view of a diagrammatic representation showing a fluidic router.

Monolithic valves can also be used to form routers, mergers, and splitters. It should be noted that although the following structures will be described in the context of three layer structures, the structures can also be implemented using four or more layers. FIG. 3 is a diagrammatic representation of a router 300. The router includes valves 301, 303, 305, and 317; pneumatic channels 331, 333, 335, 337, and 339; fluidic channels 321, 323, 325, and 327; and a diaphragm valve 309. The router pumps fluid from any input to any output depending upon which of the input/output valves are actuated at what point during the pumping cycle. Actuating two or more input valves simultaneously merges several different fluid streams into one stream at the output valve. Conversely, actuating two or more output valves simultaneously splits a single fluid stream into several different streams at the output valves.

For example, to route fluid from channel 327 to channel 321, valves 301 and 305 are held closed. Valves 317, 309, and 303 can then be used as a pump as noted above. The router includes functionality to merge and split fluid channels. To merge fluid from channels 325 and 327 into channel 323, valve 303 is held closed. To split fluid from channel 321 to channels 323 and 327, valve 301 is held closed. In yet another example, to route a fluid introduced through channel 327 to channel 325, valves 303 and 305 are held closed. Valves 317 and 301 can be opened to allow flow of a fluid through channel 327 to channel 325. A variety of arrangements are possible.

Figure 4:
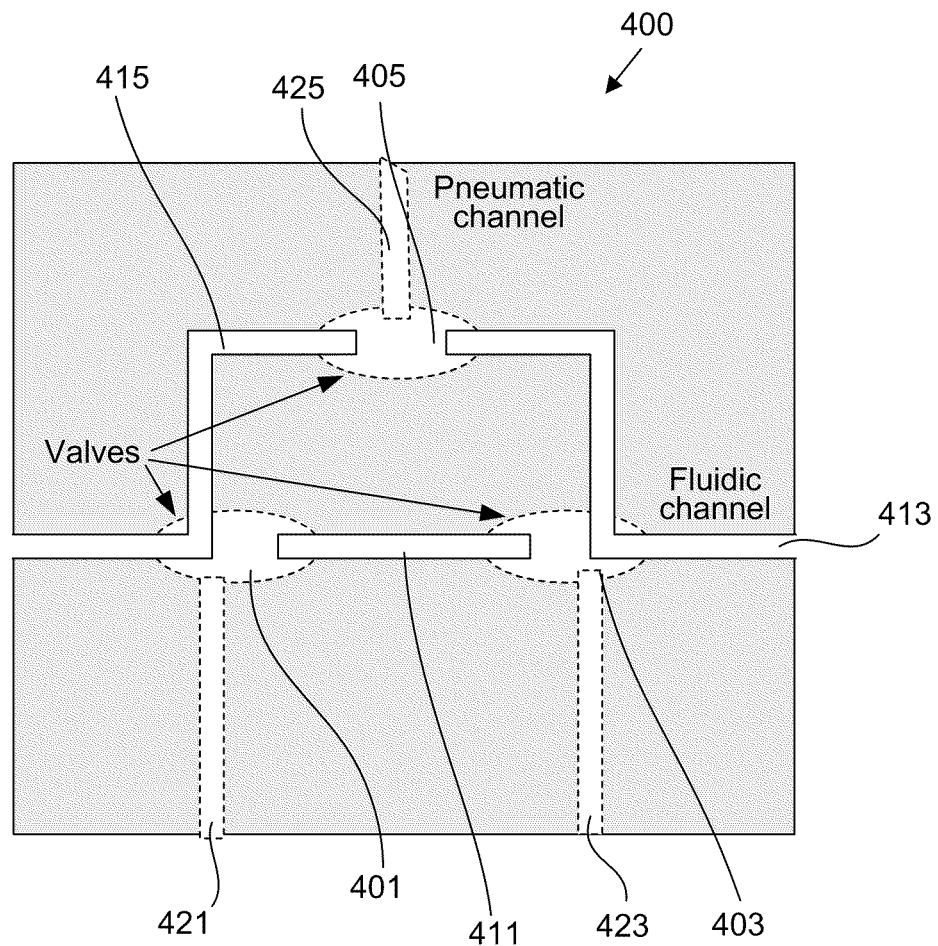
FIG. 4 is a plan view of a diagrammatic representation depicting a mixing loop.

A mixing loop can also be formed using monolithic valves. In one example, mixing can be performed by moving a fluid between two areas of a device. Mixing can be used for performing all types of on-chip operations. FIG. 4 is a diagrammatic representation of a mixing loop 400. The mixing loop or mixer includes valves 401, 403, and 405; fluidic channels 411, 413, and 415; and pneumatic channels 421, 423, and 425. Additional valved channels connect to the loop and provide fluidic access to or from the mixer. Two or more volumes of fluids can be admitted into the mixer loop through channels 413 and 415 and pumped, as noted above, in a circle until the fluids are mixed by diffusion. The mixture can then be pumped out of the mixer loop. Mixing can also be accomplished by moving a fluid back and forth between two reservoirs.

Figure 5A:
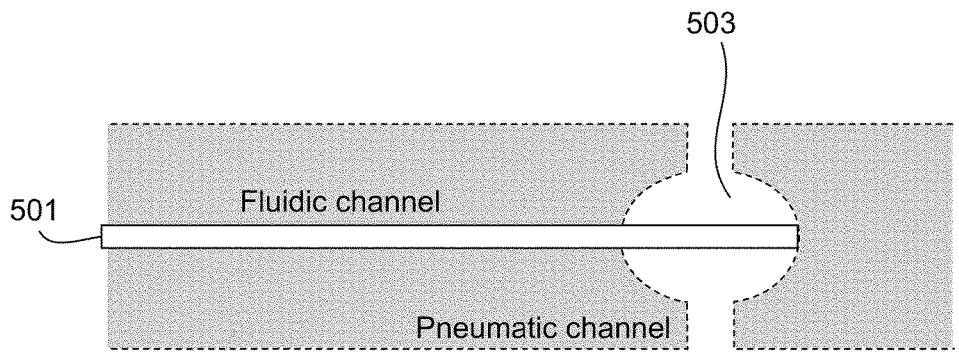
FIGS. 5A-5D are diagrammatic representations showing a fluid reservoir.
Figure 5B:
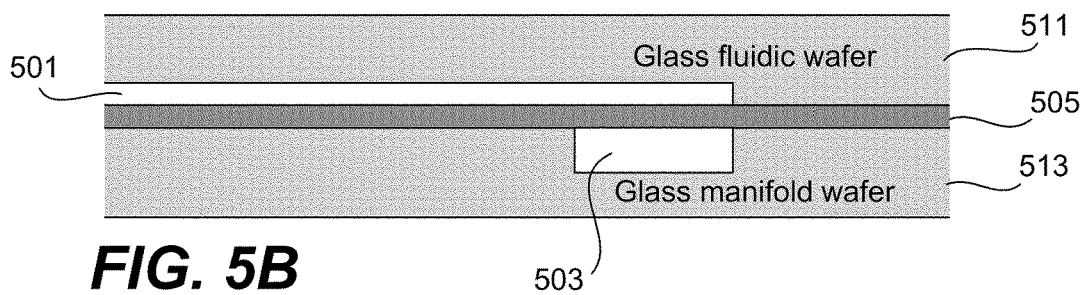
Figure 5C:
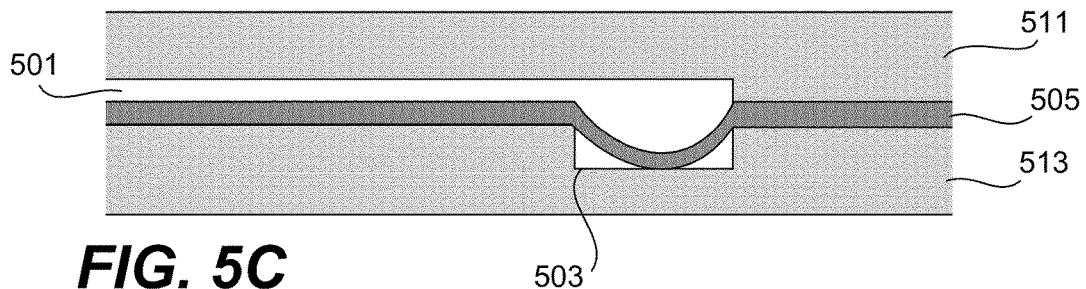
Figure 5D:
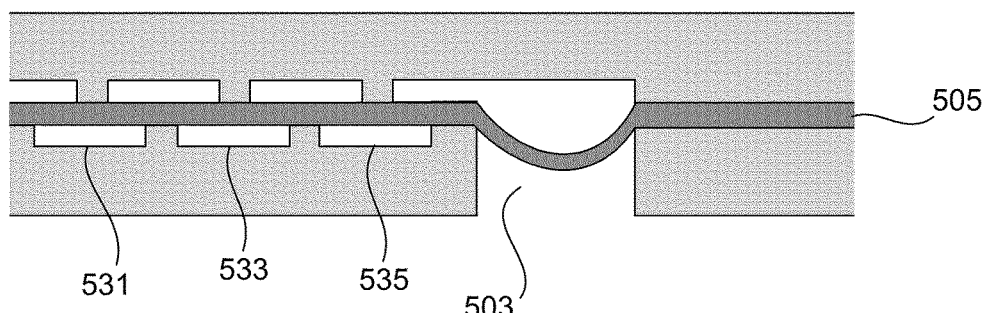

FIGS. 5A-5C are diagrammatic representations of a reservoir 500. FIG. 5A is a top view of a reservoir with an etched displacement chamber. FIG. 5B is a side view of the reservoir. FIG. 5C is a side view showing a filled reservoir. FIG. 5D is a side view of a large-volume reservoir with drilled displacement chamber and pump for autonomous filling/dispensing. The reservoir is included on a pneumatic wafer 513 sandwiching a membrane 505 with a fluidic wafer 511. The reservoir can be filled or emptied through channel 501. According to various embodiments, an open monolithic membrane valve in valve area 503 functions as a reservoir for on chip fluid storage. The size of the chamber in the pneumatic wafer 513 determines the volume of fluid stored inside the reservoir; applying vacuum fills the reservoir and applying pressure empties it.

According to various embodiments, reservoirs for storing large volumes of fluid can be fabricated by replacing the etched pneumatic chamber with a drilled hole and applying actuation pressure or vacuum directly to the hole. Alternately, a reservoir without a direct pneumatic connection can be fabricated by connecting the reservoir to a diaphragm pump. FIG. 5D shows a reservoir 503 connected to a pump. The reservoir is filled or emptied depending upon the direction of pumping and has the advantage of variable volume. In one example, pumps such as valves 531, 533, and 535 and be used to fill or dispense fluid for reservoir 503.

A monolithic membrane reservoir with one or more fluidic inputs functions as an on-chip reactor. Like the reservoir, the reactor can draw in reactants and expel products directly by using direct pressure or vacuum applied through the pneumatic manifold wafer. Alternatively, the reactor can draw in reactants and expel products indirectly using an integrated pump, mixer, and/or router structures. According to various embodiments, since the volume of the reactor is defined by the size of the chamber 503 in the pneumatic wafer, reactors with arbitrary volumes can be included at any point on a device without drastically changing the layout of structures in the fluidic wafer. Also, the reactor can be partially filled as necessary for on chip reactions that involve a variable volume of reactants.

Most elastomer membranes are gas permeable, and this property has thus far been used to simplify fluidic filling of all elastomer devices.

According to various embodiments, the gas permeability of the membrane can eliminate bubbles and air pockets. When applying an actuating vacuum to a monolithic membrane reactor, or other fluidic structure, bubbles can be eliminated from reactions that produce gas. For example, the gas permeable membrane can reduce bubbles that can form during on chip thermal cycling of PCR reactants that could result in loss of containment of the reaction mixture.

Figure 6:
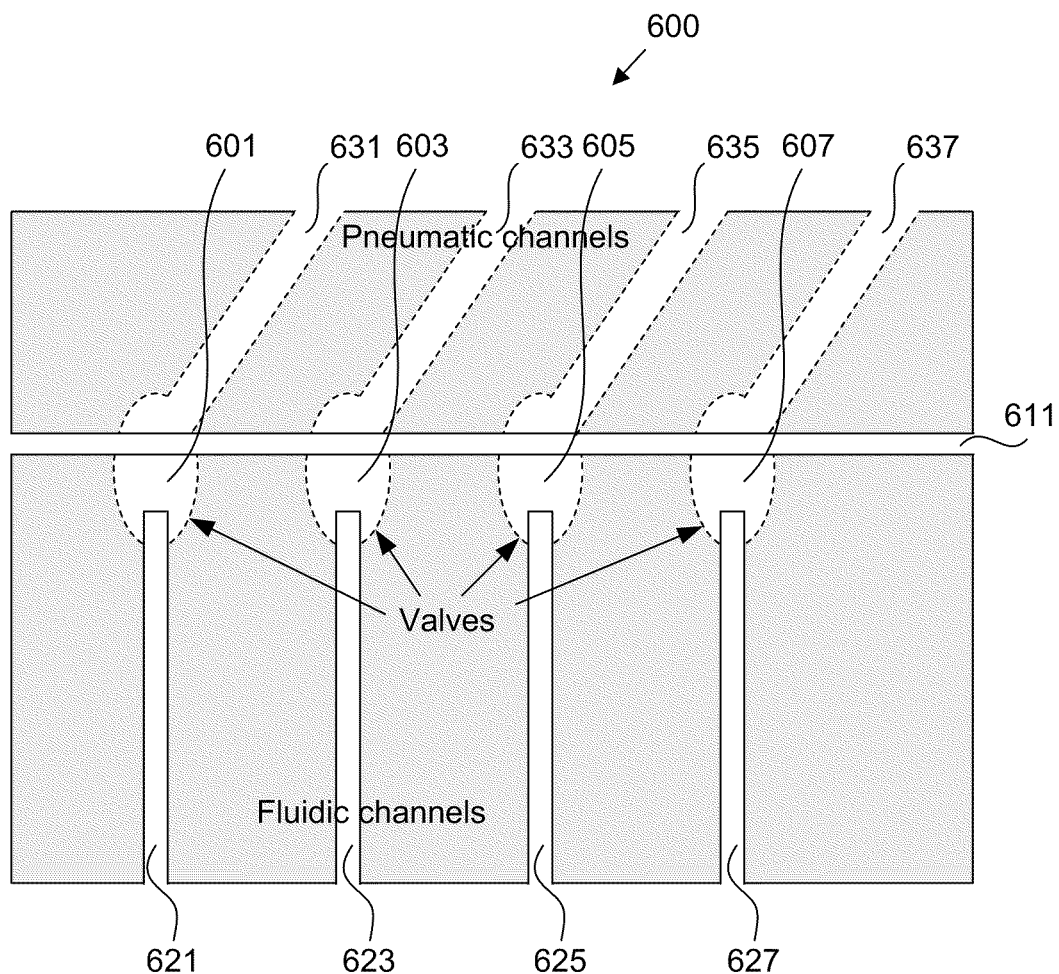
FIG. 6 is a diagrammatic representation showing bus valves.

A complex microfluidic device may include several independent modules connected to a fluidic bus. In one example, it may be useful to provide an analyte fluid to multiple different fluidic channels. In another example, a variety of reagents can be available for introduction into a microfluidic device. FIG. 6 is a diagrammatic representation of a bus valve 600 that can be used to distribute an analyte fluid. The bus valve valve 600 includes valves 601, 603, 605, and 607 that are designed to route fluids from a fluidic bus channel 611 to fluidic channels 621, 623, 625, and 627. Pneumatic channels 631, 633, 635, and 637 manage the valves for controlling distribution of the fluid. Typical bus valve implementations have dead volume on the bus side. Dead volume makes it difficult to rinse the bus completely between fluid routing operations. According to various embodiments, the techniques of the present invention provide bus valves with little or no dead volume on the bus side. This allows the bus to be rinsed completely between fluid routing operations and prevents mixing or cross contamination between different fluids during device operation.

The microfluidic device mechanisms can be fabricated using a variety of technologies. According to various embodiments, channel features are etched into glass wafers, for example, using standard wet chemical etching. Glass wafers (1.1 mm thick, 100 mm diameter) are piranha cleaned (20:1) and coated with a sacrificial (200 nm) polysilicon etch mask layer using an LPCVD furnace or sputtering system. Borofloat glass wafers or Schott D263 borosilicate glass wafers are used for devices with the three-layer or four-layer design. After polysilicon deposition, the wafers are spin-coated with positive photoresist, soft-baked, and patterned using a contact aligner. UV-exposed regions of photoresist are removed in Microposit developer. The exposed regions of polysilicon are removed by etching in $SF_6$ plasma. The wafers are etched isotropically at 7 um/min in HF solution (49% HF for the Borofloat wafers and 1:1:2 $HF:HCl:H_2O$ for the D263 wafers) until the desired etch depth is reached.

According to various embodiments, the fluidic channel wafers are etched 20 um deep for the three-layer devices and 40 um deep for the four-layer devices. The manifold wafers are etched 70 um deep for the three-layer devices and drilled at valve locations for the four-layer devices. The remaining photoresist and polysilicon is then stripped from the wafers using PRS-3000 and SF plasma, respectively. Access holes through the fluidic and manifold wafers are drilled and the wafers are again piranha cleaned.

In some examples, devices utilizing the three-layer design are assembled by applying a PDMS membrane (254 um thick HT-6135 and HT-6240, Bisco Silicones, Elk Grove, Ill.) over the etched features in the fluidic channel wafer and pressing the manifold hybrid glass-PDMS fluidic channels with valves located wherever a drilled or etched displacement chamber on the manifold was oriented directly across the PDMS membrane from a valve seat. Devices utilizing the four-layer design are assembled by first thermally bonding the fluidic channel wafer to a 210 um thick D263 via wafer with pairs of 254 um diameter drilled via holes positioned to correspond to the locations of channel gaps. The fluidic channel and via wafers are bonded by heating at 570 C for 3.5 h in a vacuum furnace (J. M. Ney, Yucaipa, Calif.). The resulting two-layer structure containing all-glass channels is then bonded to the PDMS membrane and the manifold wafer. The glass-PDMS bonds formed in this manner are reversible but still strong enough to survive the range of vacuum and pressures exerted on the device. Optionally, an irreversible glass-PDMS bond are obtained by cleaning the manifold wafer and PDMS membrane in a UV ozone cleaner (Jelight Company Inc., Irvine, Calif.) prior to assembly.

The microfluidic device mechanisms described above can be used to implement a variety of devices. The features including valves and pumps can be flexibly arranged to provide multi-channel lab-on-a-chip instruments that are able to integrate sample preparation and analysis steps into a single device. The microfluidic platform is particularly well-suited as one device capable of implementing an integrated pathogen detection system.

Conventional rapid pathogen detection systems use detection employing either Enzyme Linked Immunosorbent Assays (ELISA) or Fluorescence Immunoassays (FIA). Typically, detection involves the immobilization of an analyte specific antibody, incubation with the sample solution, and recognition with a sandwich antibody linked to an enzyme or fluorophore followed by development and detection. Immunofluorescence detection assays have also been used. However, detection limits associated with each of these assays are relatively restrictive.

The use of various formats of PCR based genetic detection and typing is also popular because of its high specificity and gain. However, even though DNA based PCR approaches are powerful, they will respond positively to both viable and nonviable pathogens, potentially producing false positives. Detection of RNA targets may be thus preferred because its rapid degradation means that live targets are required for detection.

A variety of alternative detection methods have also been proposed. Mass spectrometry methods have been developed to detect pathogens, spores, and other bioagents, by detection of neutral lipids, polar lipids and spore specific biomarkers. However, though the speed, throughput and portability of the mass spectrometry approach is not obvious and the specificity is unproven.

The detection of spores, for example anthrax, from soil, air, etc. is challenging because it is highly infective (an inhaled dose of 10,000 spores can be achieved in 10 minutes at 10 spores/L). The most advanced detection concept uses real time detection of PCR products performed in a silicon microreactor with thin film heaters and integral fluorescence excitation and detection. This system has subsequently been extended to a ten channel Advanced Nucleic Acid Analyzer (ANAA) as well as a portable version. Versions of this system are also being developed for the military and for the Post Office. A GeneXpert sample preparation system with integrated (multimicroliter) sample processing for real time PCR analysis is also being developed.

The development of portable analyzers that can rapidly perform automated and complex up front chemistries and quantitate pathogen concentrations and antibiotic resistance would be a major step forward. Similarly the ability to detect and type large numbers of samples rapidly and with very low false positives in a high throughput, multisample screening application would also be useful when large numbers of samples or potentially infected individuals need to be screened, Steps toward such automated clinical analyzers have been made. In one example, complex microfluidic circuit systems for blood clinical analyses that are essentially micro versions of the common autoanalyzer have been developed. A fully integrated analyzer (microliter volume scale) that was used for preparation of samples from blood for HIV analysis on microarrays has also been developed. This system performed a complex assay including a large number of nucleic acid steps and exploited the >100 nL dead volume pneumatic membrane valves which will be discussed in more detail below.

A lucite microfluidics cube has been developed for controlling the flow of solutions over six different immunoarray sensors that provide fluid control with a simple pressure relief system to facilitate the performance of their immunoassay with small portable systems. This format has been developed as the Raptor portable analyzer that uses integrated flow systems and fiber optic biosensor capillaries to analyze four different agents in a ten minute operation. The unique characteristics of addressable arrays have been recognized to develop an integrated stacked microlaboratory that performs automated electric field driven immunocapture and DNA hybridization array analysis. For example, following immunocapture the bacteria were released for strand displacement amplification (SDA) followed by hybridization analysis of the amplified Shiga like toxin gene. However, the multiplex sample analysis was not performed and the limits of detection was not studied.

While conventional microfabrication is done in silicon, it has been determined that for chemical and biochemical analyses, glass microfludic structures exhibit preferable chemical and electrophoretic properties and the extension to plastic structures is in progress. In the high throughput applications, the techniques of the present invention provide radial channel layouts that permit the rapid parallel analysis of 96 to 384 fragment sizing or sequencing separations in parallel. The integration of PCR directly with CE analysis on a chip is provided with enzymatic DNA digestion and affinity capture.

According to various embodiments, the microfluidic device mechanisms of the present invention allow the creation of intricate channel structures that permit the formation of complex arrays of chambers, valves and CE analysis channels. The small size of these CE channels together with the use of cross injectors facilitates the performance of very rapid, high resolution electrophoretic separations. Substantially all operations that have been performed in chromatographic columns or capillaries have also been reduced to a chip format with decreases in required sample volume and improved analysis time and sensitivity.

According to various embodiments, the pathogen detection system of the present invention has the attributes of sensitivity combined with specificity and quantitation to provide a particularly useful assay. Many pathogens are infective at $>10^3$ ingested bacteria, but *V. cholera* will not cause symptoms if less than $10^5$ organisms are orally ingested and for *B. anthracis* much lower levels are considered significant. Identifying the strain so that the pathogenic can be distinguished from the nonpathogenic, and identifying the presence of specific toxins or antibiotic resistance genes can also be critical for identifying the threat and determining the treatment. Furthermore, the ability to determine the concentration or dose of bacteria and to report this quantitatively along with the identity will distinguish important challenges from background challenges.

Figure 7:
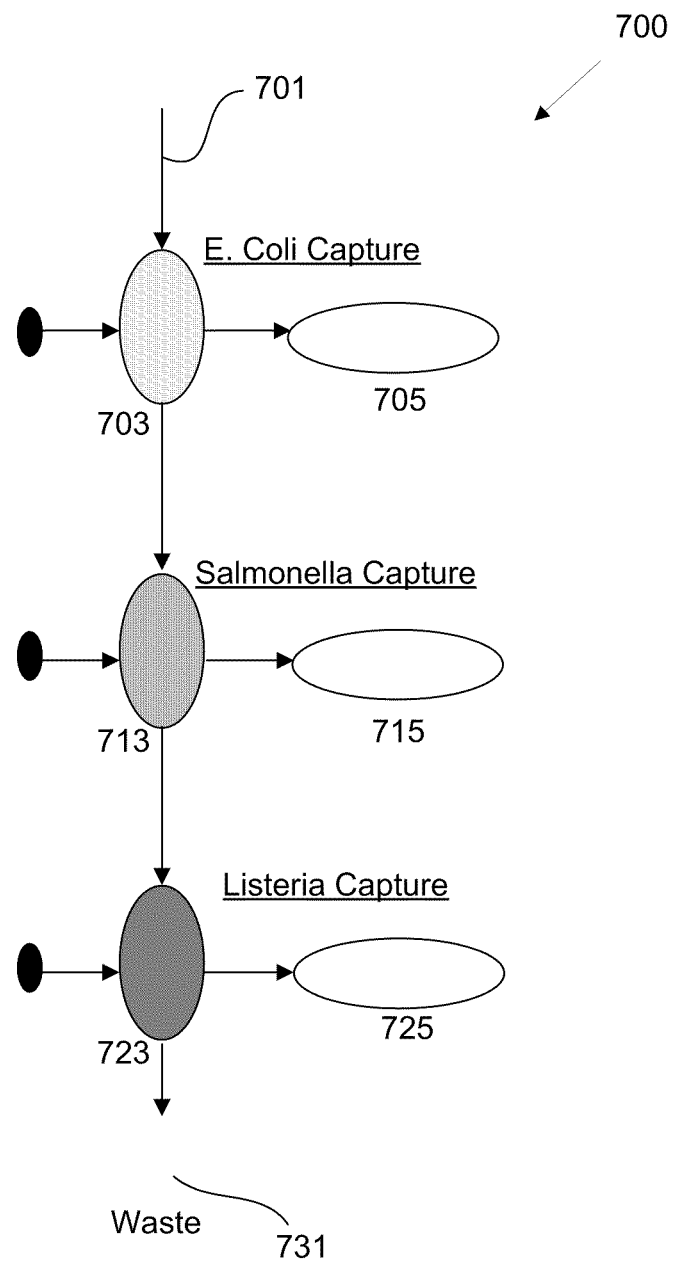
FIG. 7 is a diagrammatic representation of a pathogen detection system.

FIG. 7 is a diagrammatic representation of one example of a pathogen detection system 700. An analyte is introduced through a channel 701 into immunoaffinity capture chambers 703, 713, and 723 with waste collected at a channel 731. According to various embodiments, immunoaffinity reagents are used to capture, concentrate and stratify input bacterial mixtures into the series of separate immunological chambers 703, 713, and 723. This facile process addresses the important macro to micro interface that has previously been a barrier for the application of microfluidic systems to trace pathogen detection. The first stage of immunocapture also plays a significant role in enhancing the specificity of the assay. To achieve the enhanced sensitivity, a user of the pathogen detection system can then perform PCR based redundant confirmation of the presence of the agent and also develop methods based on specific primers or more general genotyping methods such as PCR to identify the specific strain, the presence of toxin genes and the presence of antibiotic resistance markers using DNA analysis mechanisms 705, 715, and 725. In one example, DNA analysis mechanisms 705, 715, and 725 include PCR and CE.

According to various embodiments, the immunoaffinity capture chambers 703, 713, and 723 are integrated with PCR chambers but CE mechanisms remain separate. The combination of immunocapture and nucleic acid analysis dramatically enhances the sensitivity and specificity of the individual assays.

The ability to genetically differentiate pathogenic from nonpathogenic strains is critical in many applications. The combination of immunocapture as the front end to PCR analysis provides an important purification of the input bacterial population to address concerns about the presence of PCR inhibitors often found in impure, complex "real world" samples. According to various embodiments, the pathogen detection system will be set up to perform PCR in the low cycle number (not asymptotic) regime so that quantitation of the input target population is maintained and reported. In many examples, the processed samples can then be provided for CE analysis. The use of modern microfluidic technologies will result in the production of inexpensive, rapid and robust assay systems that are small, portable, and require minimal power, resources and skill for operation.

Figure 8:
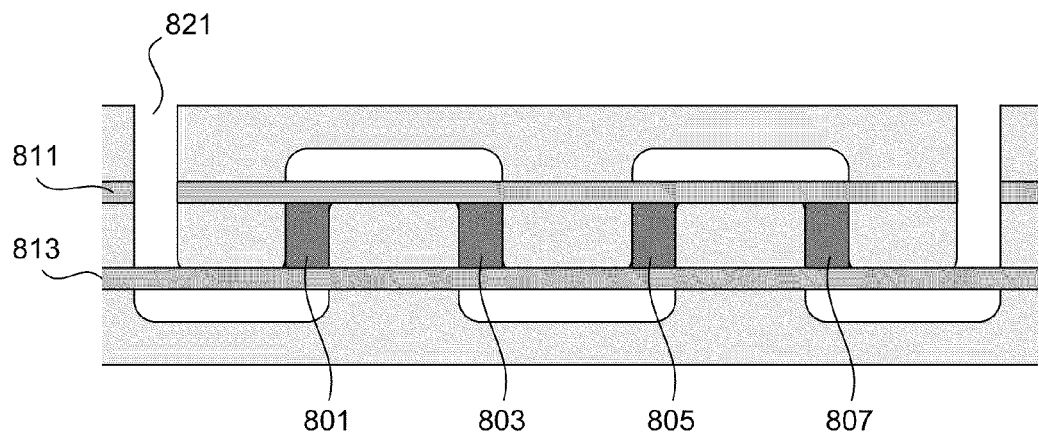
FIG. 8 is a diagrammatic representation depicting immunoaffinity capture valve mechanisms.
Figure 9:
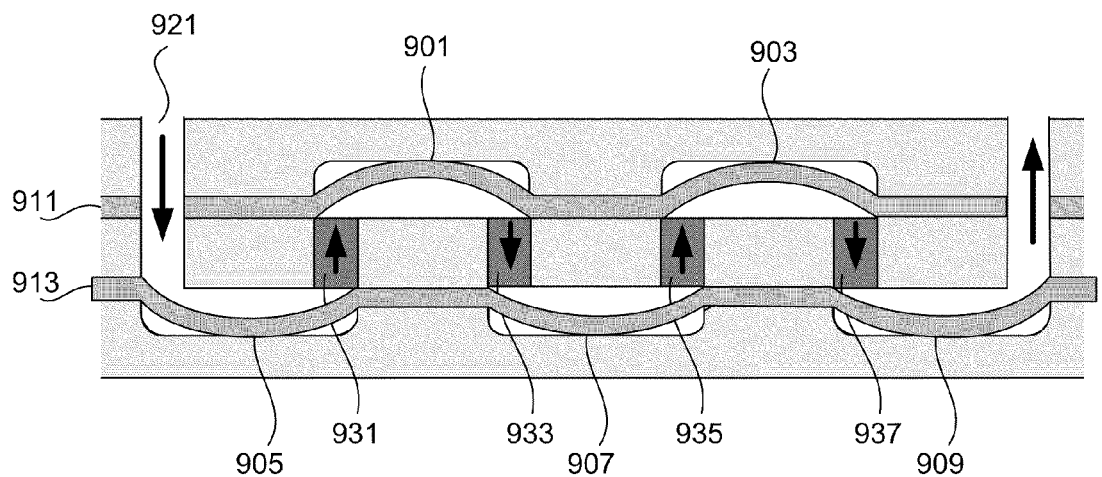
FIG. 9 is a diagrammatic representation showing immunoaffinity capture valve mechanisms.

Integrated immunoaffinity capture chambers are included in a pathogen analyzer. A variety of capture mechanisms can be used, such as frits, beads, gels, monoliths, and polymers. FIGS. 8 and 9 are diagrammatic representations showing immunocapture chambers implemented using silica frits or beads. According to various embodiments, immunocapture chambers includes a series of silica fits fabricated by filling wafer holes with a mixture of silica power and sodium silicate binder. Upon dehydration and rinsing, the silicate condenses to silica gel and an insoluble silica frit is formed at 801, 803, 805, and 807.

According to various embodiments, each silica frit formed in a 1.1 mm thick glass wafer is 1 mm in diameter. The immunocapture chambers are associated with a channel 821 for introducing and evacuating an analyte. The in-wafer fits can easily be integrated into devices containing membranes 811 and 813 and valve and pump structures. In FIG. 8, the four silica fits 801, 803, 805, and 807 are sealed shut by membranes 811 and 813. The large silica surface of each frit is suitable for chemical derivatization by a wide variety of organosilane reagents. To further simplify device fabrication, the monolith wafer can be chemically derivatized prior to non-thermal PDMS bonding to the rest of the device.

In one example, mechanisms such as frits or beads 1.5 um are provided into a capture chamber to allow for capture of many macro species such as spores and bacteria. Solid-phase capture of many macro-species is known to those of skill in the art and is well characterized in Weimer, B. C., M. K. Walsh, C. Beer, R. Koka, and X. Wang, 2001 Solid Phase Capture Of Proteins, Spores, and Bacteria. *Appl Environ. Microbiology*, 67:1300-1307. In some examples, to utilize bead reagents for capture, the chamber is modified with a weir structure to provide a bead stop, as well as a bead introduction channel. Electrokinetic bead bed packing and weir bead trapping is known to one of skill in the art. Alternatively, immunofunctionalized magnetic beads may be introduced into a chamber without a weir.

FIG. 9 is a diagrammatic representation showing open valves with the monoliths no longer sealed. According to various embodiments, pneumatic vacuum pressure is applied at regions 901, 903, 905, 907, and 909 to allow flow of an analyte along channel 921 through the frits 931, 933, 935, and 937. Any number of frits may be included in a fabricated device.

FIG. 10A is a diagrammatic representation showing capture of an analyte. According to various embodiments, a pump 1000 including three membrane valves 1001, 1003, and 1005 is used to pump an analyte solution containing oligonucleotides, proteins, cells, etc., through the series of immunocapture chambers.

Chambers can use a variety of mechanisms for capturing a target of interest. Anything of interest configured for capture in an immunocapture chamber is referred to herein as a target. The fluid or substance carrying the target is referred to herein as an analyte. In one example, the target is *Salmonella* or *Listeria* carried in a fluid analyte.

In other examples, each capture chamber is filled with a viscous polymeric matrix containing oligonucleotide probes to selectively bind the target molecules. In the case of DNA analysis, Sanger DNA sequencing extension products, including primers and polymerase reagents in a high salt concentration, are electrophoresed through an immunocapture chamber containing the immobilized acrylamide matrix containing the covalent oligonucleotide probe. The capture sequence is chosen so that only DNA amplification products are captured by the probe, but the primers and polymerase reagents, along with salts, pass through the device. This is not unlike the need to purify target molecules from complex, dirty mixtures that will be encountered in point of care analyses.

An alternative approach for the preparation of microcapture chambers with functionalized polymeric capture matrices includes the preparation of monoliths with pores in the range of 10-20 um, and the preparation of chambers with large microfabricated elements (ca. 100 um) surface modified by a thin crosslinked layer of functional polymer. This approach is useful as beads are sometimes found difficult to pack in capture chambers and bead beds are often not sufficiently mechanically stable for routine operation. According to various embodiments, molded blocks of porous (10-20 um) surface functionalized polymer monoliths are formed directly within the capture chambers by photo polymerization of a precursor mixture including monomers and porogenic solvents.

Since the polymerization process is accomplished using UV light, the porous polymer can be formed in any desired area of the microfluidic device using photolithography. The kinetics of such a "microlithographic" polymerization process using glass chips filled with a precursor mixture has been characterized and is known to one of skill in the art as shown in Yu, C., F. Svec, and J. M. J. Frechet 2000. Towards stationary phases for chromatography on a microchip: Molded porous polymer monoliths prepared in capillaries by photoinitiated in situ polymerization as separation media for electrochromatography. *Electrophoresis*, 21:120-127 and Yu, C., M. Xu, F. Svec, and J. M. J. Frechet 2002. Preparation of monolithic polymers with controlled porous properties for microfluidic chip applications using photoinitated free radial polymerization. *J. Polymer Sci.*, 40:755. Similarly the precise location of the monolithic material on the device as well as its surface chemistry can be controlled as is known to one of skill in the art as shown in, Rohr, T. C, C. Yu, H. M. Davey, F. Svec, and J. M. J. Frechet 2001. Simple and efficient mixers prepared by direct polymerization in the channels of microfluidic chips. *Electrophoresis*, 22:3959. Control over porous properties of the monolithic polymers can be achieved by adjusting the composition of the porogenic solvents.

Whether a monolith or a surface with microfabricated elements is used, the same grafting approach can be used to introduce the desired binding elements. Since the goal is to immobilize antibodies on the pore surface of these monoliths, the grafted chemistries are specified to readily react with biopolymers. In one example, units of 2-vinyl-4,4-dimethylazlactone incorporated into a surface graft can react rapidly with proteins. Such mechanisms are known to one of skill in the art as shown in Peterson, D. S., T. Rohr, F. Svec, and J. M. J. Frechet. 2002. Enzymatic microreactor-on-a-chip: protein Mapping using trypsin immobilized on porous polymer monoliths molded in channels of microfluidic devices. *Anal. Chem.*, 74:4081:4088. The surface to be modified (porous monolith, or microfabricated elements) can be immersed in a monomer solution and the device can be irradiated by UV light to achieve grafting in preselected areas. The extent of surface functionalization is controlled by the concentration of the monomer in the reaction solution, the irradiation time, and the intensity of the UV light.

In other embodiments, trypsin is immobilized on porous polymer monoliths consisting of 2-vinyl-4,4-dimethylazlactone, ethylene dimethacrylate, and acrylamide or 2-hydroxyethyl methacrylate. The azlactone functionalities react readily with amine and thiol groups of the enzyme to form stable covalent bonds. In some examples, the optimized porous properties of the monoliths lead to very low back pressures enabling the use of simple mechanical pumping to carry out both the immobilization of the enzyme from its solution and the subsequent analyses of substrate solutions. The Michealls-Menten kinetic characteristics of the reactors can be probed using a low molecular weight substrate such as N-a-benzoyl-L-arginine ethyl ester.

The effects of immobilization variables such as the concentration of trypsin in solution and percentage of azlactone functionalitiestles in the in the monolith, as well as the effect of reaction time on the enzymatic activity, and of process variables such as substrate flow velocity and residence time in the reactor, were studied in detail. The proteolytic activity of the enzymatic microreactor on chip was demonstrated at different flow rates with the cleavage of fluorescently labeled casein used as a substrate. The excellent performance of the monolithic microreactor was also demonstrated with the digestion of myoglobin as the fast flow rate of 0.5 uL/min, which affords a residence time of only 11.7 s. The digest was then characterized using MALDI-TOFMS, and 102 out of 153 possible peptide fragments were identified giving a sequence coverage of 67%.

An enormous effort has been directed toward the development of new micorfabricated analytical devices and their integration to create micro total analytical systems (Ptas). These systems offer the promise of increased throughput, lower sample and reagent consumption, smaller size, and lower operating costs than full size instrumentation, Among the various applications of microfluidic devices, analytical techniques such as electrophoresis, electrochromatography, assays involving enzymes, and immuno-assays have already been demonstrated in this format. Despite the undeniable success of microfluidic chip technologies, some problems persist. For example, the vast majority of microfluidic chips feature open channel architecture. Consequently, these channels exhibit rather small surface-to-volume ratios. They may be a serious problem in applications such as chromatographic separations, solid-phase extraction, and heterogeneous catalysis that rely on interactions with a solid surface. Since only channel walls can be used to provide the desired interactions, the microdevice can only handle minute amounts of compounds.

FIG. 10B is a diagrammatic representation showing use of the two-dimensional analysis system. After the monoliths 1027 capture targets provided by the pump with valves 1001, 1003, and 1005, the monoliths 1027 are sealed. In one example, each chamber is then heated to melt the double stranded DNA and drive off the single stranded DNA product. According to various embodiments, the purification takes place in 120 seconds, and a 200 fold concentration to only 20 nL from an initial volume of 3 uL can be achieved. Each line 1011, 1013, 1015, 1017, 1019, and 1021 includes valves for controlling or pumping captured targets for additional analysis steps.

In one example, captured targets are provided for PCR and CE analysis on the test device. Captured targets can be released for DNA analysis using mechanisms such as heat or a change in pH. The basic features of such an integrated test device include: 1) an immunocapture chamber etched into a glass substrate with a microfabricated heater and temperature sensor; 2) a polymerase chain reaction chamber of 100

300 nL for amplification of DNA obtained from lysing the cells of interest; and 3) a capillary electrophoresis microchannel etched into the glass substrate for separation and detection of the PCR amplicons.

An optional fourth item, an integrated DNA preconcentration/clean-up chamber, can also be added to the device for purification of the released pathogen genomic DNA or for desalting and preconcentration of the amplified DNA before injection onto the CE microchannel if needed. Although previous studies have shown that PCR amplicons can be directly injected onto CE microchannels for successful analysis, potentially obviating the necessity of such additional complexity, such purification may be necessary to obtain high quality electropherograms. This amplicon purification could be enabled by using oligonucleotide capture matrix chemistries. If it is necessary to purify the genomic DNA, a clean-up chamber could be filled with carboxylated silica beads and used as a general capture matrix for bacterial DNA before PCR.

Figure 11:
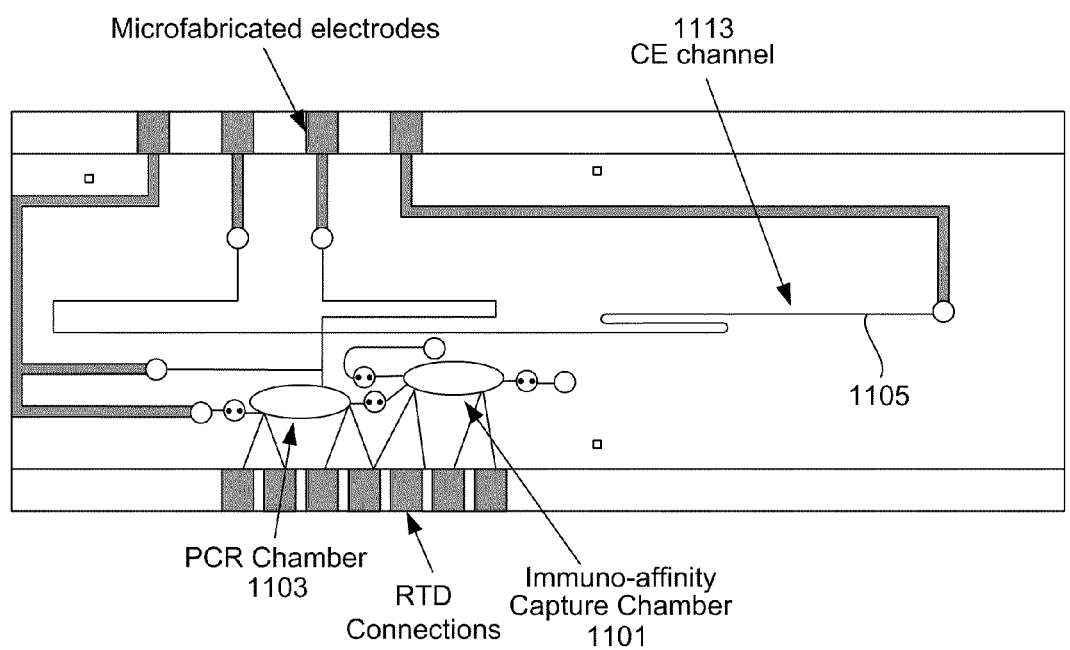
FIG. 11 is a diagrammatic representation showing PCR and CE that can be integrated with immunoaffinity capture.

One approach to integration is simply to fabricate immunocapture, template purification, PCR, amplicon clean-up, and CE as separate modules on a glass chip. The modules would then be interfaced with each other using microchannels and various PDMS valve structures. A schematic of a pathogen analysis chip configured with separate immunocapture and PCR reactors is presented in FIG. 11. The integrated pathogen detection system includes an immunoaffinity capture chamber 1101. An analyte is introduced into the pathogen detection system through the immunoaffinity capture chamber 1101. A PCR chamber 1103 is coupled to the immunoaffinity capture chamber 1101 and receives targets captured by the immunoaffinity capture chamber 1101. A CE channel 1105 is coupled to the PCR chamber 1103 for further analysis. Microfabricated electrodes 1113 are operable to provide voltage differentials. A heater (not shown) coupled to the immunocapture chamber and/or the PCR chamber is also provided. A variety of valves control the flow an analyte through the integrated system. According to various embodiments, the valves are monolithic valves.

Although providing immunocapture, PCR, CE and clean-up as separate modules on a device is a reasonable strategy, the capture efficiency, PCR efficiency and high sensitivity separation and detection of DNA fragments that are facilitated according to various embodiments suggest that a less complex device can be used. While immunocapture and PCR could be performed in separate chambers, in one example, immunocapture and PCR can be combined to simplify the device and the process. In this example, PCR can be successfully conducted from solid substrates and from solid phase immunocapture reagents. In one example, PCR can be performed using immuno-labeled beads.

Figure 12:
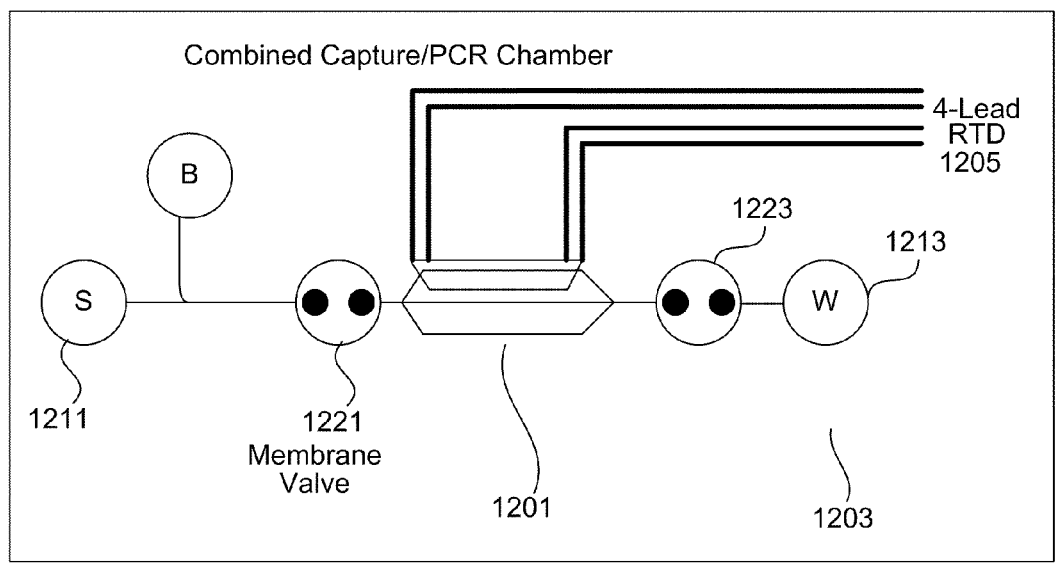
FIG. 12 is a diagrammatic representation of a combined immunocapture and PCR chamber.

FIG. 12 is a diagrammatic representation showing a combined immunocapture and PCR chamber 1201. According to various embodiments, the combined chamber has integrated resistance heating mechanism (not shown) and a resistance temperature detector (RTD) 1205 fabricated within the nanoliter chamber. In some examples, an analyte is introduced through an input 1211 through a membrane valve 1221. Pathogens of interest are immobilized within the chamber 1201 using pressure driven flow and waste is collected through a valve 1223 at an output 1213. After pathogens are immobilized, the chamber 1201 is flushed with buffer to remove loosely adhered cells or non specifically bound agents.

PCR buffer is introduced either through the original sample inlet 1211 or through a separate dedicated inlet Depending on the pathogen of interest in the chamber 1201, a chemical lysis agent can be included directly into the PCR buffer. After introduction of the lysis reagent and/or PCR buffer, the integrated heater 1203 in the capture/PCR chamber is used to raise the temperature of the sample to a temperature at which the pathogens are simultaneously released from the capture matrix and, depending on the class of agent, lysed.

The simplest and often most effective lysis method is simply performing heating/cooling cycles. Gram negative bacteria and some eukaryotic cells, with their thinner outer membranes, are more susceptible to lysis using either heat alone or heat with a small concentration of chemical lysis solutions. In some cases, such as for spores or gram positive bacteria, use of a more aggressive lysis agent that would interfere with the PCR may be necessary. For example, lysozyme, proteinase K, lysostaphin, and mutanolysin are commonly required separately or in tandem to lyse some recalcitrant gram positive Staphylococcal and & Streptococcal strains. In these cases, the use of a separate immunocapture chamber and the addition of a clean-up/preconcentration chamber allows for intermediate capture of DNA after cell lysis but before PCR amplification.

In this scenario, following capture and lysis, the extracted DNA can be electrophoretically driven into the cleanup chamber for storage by adsorption to carboxyl beads. The purified DNA can be released from the clean-up chamber using heat or variations in ionic strength and electrophoretically transported into the PCR chamber for amplification. Once the DNA from the lysed cells is presented to the chamber with PCR buffer, PCR can be performed directly on the released genetic material using the microfabricated heater and temperature sensor.

It should be noted that in some instances, the combined use of a single chamber for both capture and PCR is problematic because of complexity or PCR inhibition. In these particular instances, the two stages can simply be separated. In some examples, this may be done if the presence of the capture matrix or beads inhibits the PCR reaction or if the input sample brings in PCR inhibitors that can not be washed out or neutralized. In this case, the released DNA could be pumped or electrophoresed from the lysed bacteria in the capture chamber to a separate PCR reactor for analysis.

Upon completion of PCR, the amplicons can be directly injected onto a CE microchannel for separation and detection, either using intercalating dye in the separation matrix or fluorescently labeled primers and a denaturing separation matrix depending on the desired resolution. In some instances, a DNA clean-up chamber is introduced to desalt and concentrate the amplified DNA prior to injection onto the CE microchannel. Clean-up is accomplished by electrophoresing the amplified DNA into the clean-up chamber where it is bound to carboxylated beads or to an oligonucleotide capture matrix (capture oligos complementary to the desired targets). Binding followed by washing and temperature dependent release using a micro heater is followed by electrophoresis of the concentrated and desalted PCR amplicons through the injection cross of the CE microchannel for separation and detection.

Figure 13A:
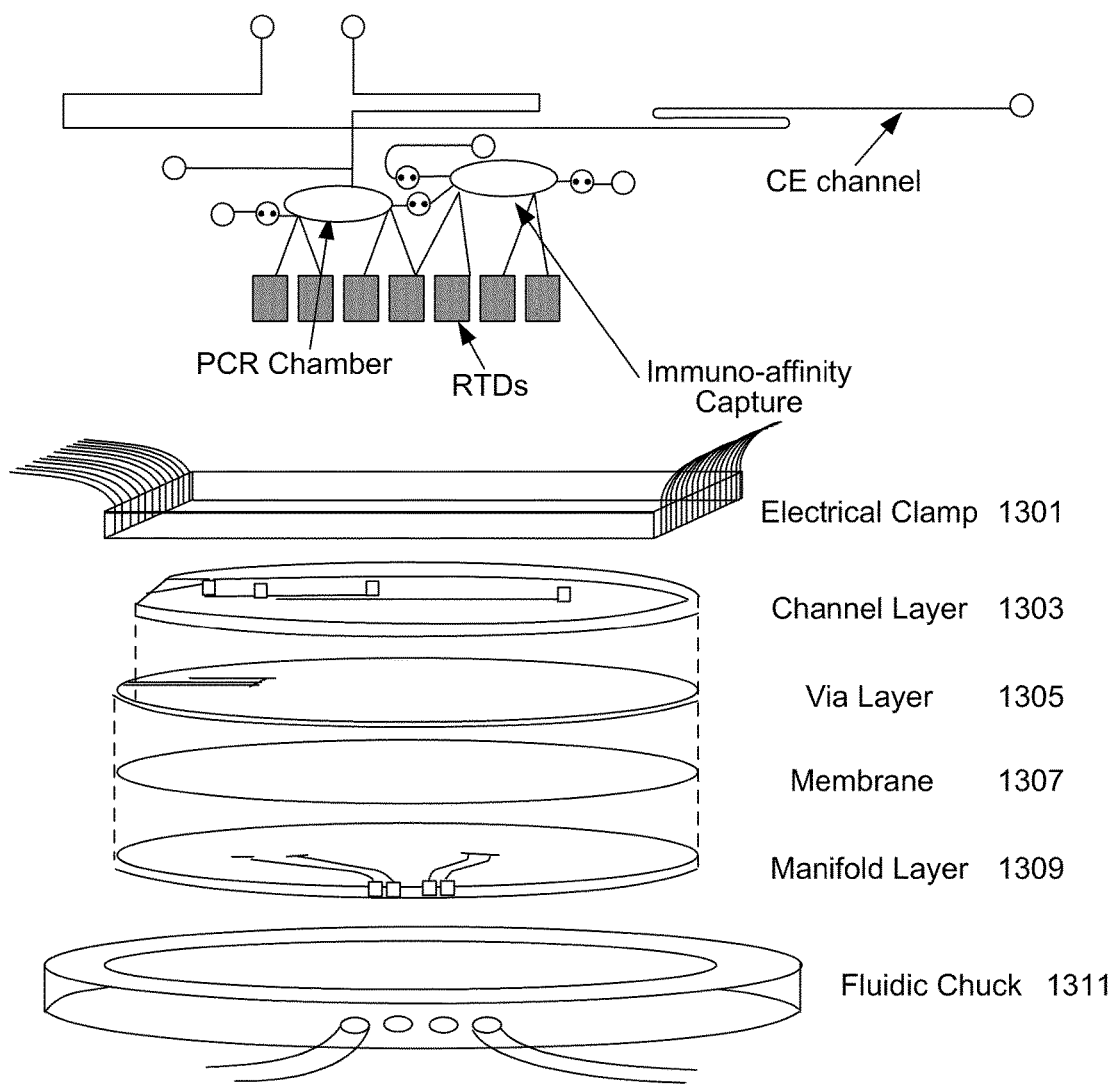
FIG. 13A is a diagrammatic representation of a pathogen detection system.

The device configuration for using monolithic membrane valves to build a pathogen detection and analysis system can be varied substantially. FIG. 13A is a diagrammatic representation showing one example of a design for the pathogen detection and analysis system. The design includes three glass layers, including a channel layer 1303, a via layer 1305, and a manifold layer 1309. A PDMS membrane layer is provided between a via layer 1305 and a manifold layer 1309. The manifold layer 1309 includes mechanisms allowing vacuum pressure to be applied to the membrane 1307 to allow control of valve mechanisms.

Electrical connections are provided on a layer 1301 and a manifold chuck layer is included at layer 1311. The channel layer 1303 includes the immunocapture/PCR/clean-up chambers and CE microchannels; as well as the heaters on the top surface of the wafer. According to various embodiments, the channel layer 1303 is thermally bonded to a thin glass wafer 1305 containing drilled glass holes that act as valve vias. A PDMS valve/pump membrane 1307 is either reversibly or irreversibly bonded to this multiple layer stack. The bottom etched manifold layer 1309 conveys vacuum or pressure to the valves and pumps on the device.

The use of existing thin film technology to create the temperature control elements presents a viable first approach to construction of test devices. However, the fabrication complexity of the device can be reduced through the use of indium tin oxide (ITO) heaters. ITO heaters are noted, for their low resistivity, optical transparency, and compatibility with glass substrates. These heaters can be deposited on the same wafer as the temperature sensors, obviating the need for backside fabrication and electroplating to form the heaters. The heaters can be placed directly within the chambers for optimal thermal transfer or they can be placed against the chambers to conduct thermal energy through a glass wafer. The optical transparency of ITO also allows routing of electrical heater leads over fluid microchannels without interfering with visualization or detection of sample or PCR amplicons.

Figure 13B:
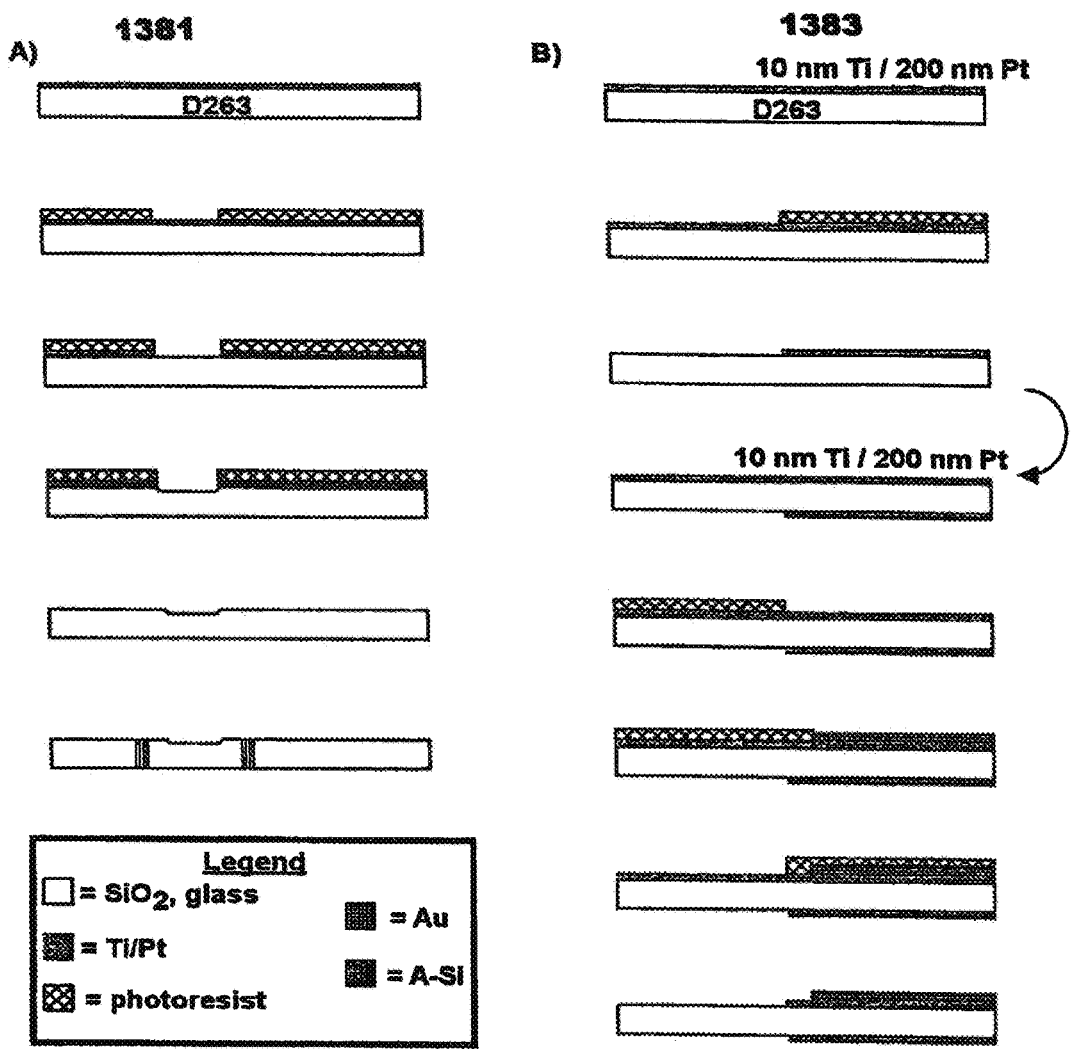
FIG. 13B is a diagrammatic representation showing microfabrication stages.

FIG. 13B is a diagrammatic representation showing a microfabrication process according to various embodiments. Microfabrication processes are shown at 1381 and 1383. In some examples, glass wafers (550 μm thick D263 available from Schott of Yonkers, N.Y.) are cleaned before sputter deposition of a 2000 Å layer of amorphous silicon on one side by DC magnetron sputtering available from UHV Sputtering of San Jose, Calif.). Photoresist available from Shipley 1818 of Marlborough, Mass. is spun on and photolithographically patterned using a contact aligner available from Karl Suss of Waterbury Center, Vt. and the underlying silicon etch mask can be selectively removed using SF6 in a parallel-plate reactive ion etching (RIE) system available from Plasma Therm of St. Petersburg, Fla.

In some examples, the fluidic channels, electrophoresis channels, and PCR chambers are etched to a depth of 36 μm in 49% hydrofluoric acid. Reservoir access holes (1.5 mm diameter) and fluidic via holes (0.020" diameter) for the PDMS valves are drilled using a CNC mill available from Flashcut CNC of Menlo Park, Calif. with diamond-tipped drill bits. The wafer is then diced using a wafer dicing saw to form two 20 mm×75 mm slides.

To form the RTDs and electrodes, a 550 μm-thick D263 wafer can first be sputtercoated with 200 Å of Ti and 2000 Å of Pt (UHV). Thick photoresist available from Shipley (SJR 5740) of Marlborough, Mass. is spun on and patterned using a contact aligner available from Suss Microtec of Waterbury Center, Vt. According to various embodiments, the photoresist is hard baked at 70° C. for 2 hours. The metal can be etched using hot aqua regia (3:1 HCl:HNO3, 90° C.) to form the RTD elements. The integrated heaters are formed by first depositing a multi-layer thin film of 200 Å of Ti and 2000 Å of Pt on the backside of the RTD wafer using RF sputtering available from Perkin Elmer of Wellesley, Mass. Thick photoresist is spun on the side, the wafer is patterned using a backside contact aligner (Suss), and hard baked. Gold is electrodeposited onto the Ti/Pt seed layer at 4.3 mA/cm2 for 23 minutes to a 5 μm thickness using a gold sulfite plating solution available from Technic (TG 25 E) of Anaheim, Calif. to form the heater leads.

According to various embodiments, the photoresist is removed and the backside is re-patterned using thick photoresist. The heating elements are etched into the Ti/Pt seed layer using an ion beam etching system available form Veeco Instruments of Plainview, N.Y. The RTD/heater wafer is diced into two 25 mm×75 mm slides (Disco). In some examples, the drilled channel wafer is thermally bonded to the RTD/heater wafer using a programmable vacuum furnace available from Centurion VPM, J. M. Ney, of Yucaipa, Calif.

Although, a single immunocapture, PCR, and CE system can be included on a substrate, the techniques of the present invention recognize that it may be efficient to develop a parallel immunocapture, PCR, and CE system for use in clinical diagnostics. In one example, a portable pathogen analyzer includes three serial immunocapture/PCR systems targeted towards the detection of three different pathogens in a sample. The parallelization of the fluidics control systems, electrical circuitry for heaters, temperature sensors and electrophoresis for three systems is straightforward and a single microscope slide has sufficient surface area to fabricate three fully parallel systems.

Figure 14:
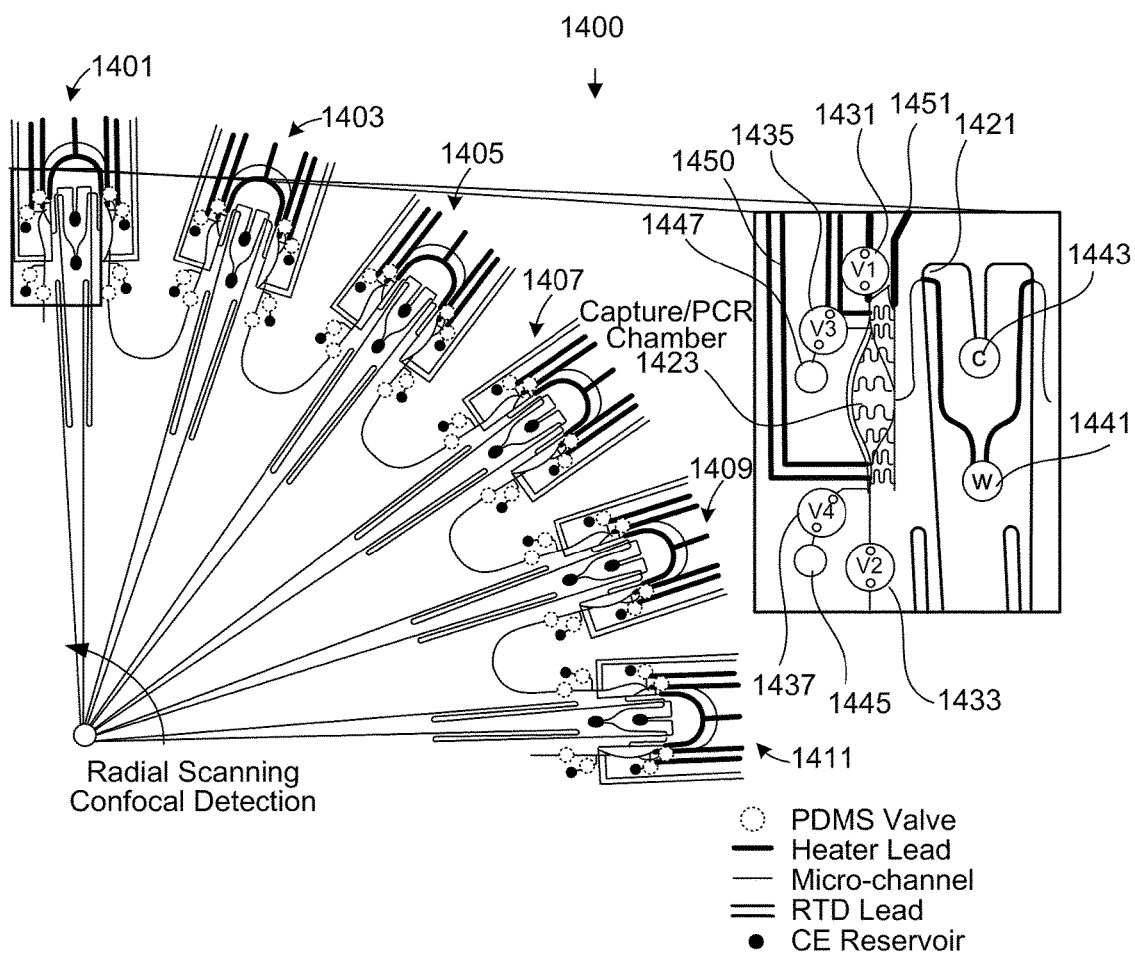
FIG. 14 is a diagrammatic representation of a radial array of pathogen detection systems.

In another example, a massively parallel immunocapture/PCR system for use in clinical diagnostics is provided. The ability to analyze multiple distinct agents across multiple individuals or groups of individuals provides a powerful method for identifying and epidemiologically tracking infectious agents. FIG. 14 is a diagrammatic representation of a portion of a radially parallel immunocapture/PCR device 1400. Any system or device having multiple immunocapture and DNA analysis mechanisms arranged about a circular axis is referred to herein as a radially parallel device.

According to various embodiments, the design includes an array of pairs of analyzers each of which includes a unique immunocapture/PCR chamber 1423 integrated with a CE analyzer. The sample travels serially through all chambers within a given subset of the device, allowing for serial capture of multiple agents. Separate subsets 1401, 1403, 1405, 1407, 1409, 1411 of the device are capable of analyzing different substances in parallel. Reservoirs 1447 and 1445 provide bead input and bead waste. Reservoirs 1443 and 1441 are the common capillary electrophoresis cathode reservoir and waste reservoir, respectively.

The chambers are interconnected for cascaded immunoaffinity capture. Valves 1431 and 1433 seal the chamber on the cascade loop. Valves 1435 and 1437 seal the chamber from bead introduction and waste channels. CE microchannels are connected to a common central anode for detection using a proven rotary confocal fluorescence scanner (not shown). A parallel array of combined capture chambers 1423 and heaters with leads 1451 and the development of robust arrays of valves and pumps are provided. Since the heaters and temperature sensors associated with chambers 1423 are operating in parallel on the analysis channels, the use of simple ring heaters are more than adequate. Thus the individual heaters and temperature sensors are no longer necessary for providing an efficient and effective parallel pathogen detection system Although many of the components and processes are described above in the singular for convenience, it will be appreciated by one of skill in the art that multiple components and repeated processes can also be used to practice the techniques of the present invention.

While the invention has been particularly shown and described with reference to specific embodiments thereof, it will be understood by those skilled in the art that changes in the form and details of the disclosed embodiments may be made without departing from the spirit or scope of the invention. For example, the embodiments described above may be implemented using a variety of materials. Therefore, the scope of the invention should be determined with reference to the appended claims.

What is claimed is:

1. A method for controlling fluid flow on a microfluidic device, the method comprising:
providing a microfluidic device comprising one or more elastomer membranes sandwiched between a pneumatic layer and a fluidic layer, wherein the fluidic layer comprises a plurality of fluidic channels, each of which comprises of a discontinuity, and a plurality of via holes at the discontinuity, wherein the pneumatic layer comprises a first surface including at least one pneumatic channel facing an elastomer membrane and valve areas aligned with said discontinuities, the fluidic layer comprising a second surface including the plurality of via holes facing the one or elastomer membranes;
controlling fluidic flow across a fluidic channel by varying pneumatic pressure in a pneumatic channel thereby causing an elastomer membrane to deflect at a discontinuity of the fluidic channel to modulate a flow of a fluid volume from one side of the discontinuity, through the plurality of via holes, to the other side of the discontinuity; and
varying pneumatic pressure in one pneumatic channel to thereby cause one or more elastomer membranes to deflect at discontinuities of a plurality of fluidic channels to modulate flow of a plurality of fluid volumes in the plurality of fluidic channels.

2. The method of claim 1, wherein the microfluidic device further comprises an input valve, an output valve and a diaphragm valve, the input valve, output valve and diaphragm valves being in series and wherein the method further comprises opening the input valve and closing the output valve by varying pneumatic pressure to the one or more of the elastomer membranes, opening the diaphragm valve and closing the input valve by varying pneumatic pressure; and opening the output valve and closing the diaphragm valve, wherein closing the diaphragm valve pumps fluid through the open output valve.

3. The method of claim 1, wherein causing an elastomer membrane to deflect at a discontinuity of the fluidic channel to modulate a flow of a fluid volume from one side of the discontinuity, through the plurality of via holes, to the other side of the discontinuity comprises causing the elastomer membrane to deflect away from the discontinuity to provide a path for the fluid volume across the discontinuity.

4. The method of claim 1, wherein causing an elastomer membrane to deflect at a discontinuity of the fluidic channel to modulate a flow of a fluid volume from one side of the discontinuity, through the plurality of via holes, to the other side of the discontinuity comprises causing the elastomer membrane to deflect toward from the discontinuity to prevent flow of the fluid volume across the discontinuity.

5. The method of claim 1, wherein the fluidic layer is gas impermeable.

6. The method of claim 1, further comprising varying pneumatic pressure in a plurality of pneumatic channels to thereby cause one or more elastomer membranes to deflect modulate flow of a plurality of fluid volumes in the plurality of fluidic channels.

7. The method of claim 1, further comprising deflecting one or more of the elastomer membranes within a displacement chamber in the pneumatic layer to thereby form a fluid reservoir in a fluidic channel.

8. The method of claim 1, wherein varying the pneumatic pressure in the pneumatic channel comprises applying vacuum to the pneumatic channel.

9. The method of claim 1, wherein varying the pneumatic pressure in the pneumatic channel comprises applying pressure to the pneumatic channel.

10. The method of claim 1, wherein varying the pneumatic pressure in the pneumatic channel comprises applying pressure or vacuum to a port in the pneumatic layer.

11. The method of claim 1, wherein the pneumatic layer is plastic.

12. The method claim 1, wherein the fluidic layer is plastic.

13. The method of claim 1, wherein the microfluidic device has only one elastomeric layer.

* * * * *